(12) United States Patent
Burnett et al.

(10) Patent No.: US 7,109,207 B2
(45) Date of Patent: Sep. 19, 2006

(54) SPIROSUBSTITUTED PIPERIDINES AS SELECTIVE MELANIN CONCENTRATING HORMONE RECEPTOR ANTAGONISTS FOR THE TREATMENT OF OBESITY

(75) Inventors: Duane A. Burnett, Bernardsville, NJ (US); Wen-Lian Wu, Edison, NJ (US); Thavalakulamgara K. Sasikumar, Westfield, NJ (US); Martin S. Domalski, Verona, NJ (US)

(73) Assignee: Schering Corporation, Kenilworth, NJ (US)

( * ) Notice: Subject to any disclaimer, the term of this patent is extended or adjusted under 35 U.S.C. 154(b) by 93 days.

(21) Appl. No.: 10/607,051

(22) Filed: Jun. 26, 2003

(65) Prior Publication Data

US 2004/0024002 A1 Feb. 5, 2004

Related U.S. Application Data

(60) Provisional application No. 60/391,813, filed on Jun. 27, 2002.

(51) Int. Cl.
*A61K 31/438* (2006.01)
*C07D 401/04* (2006.01)
*C07D 417/04* (2006.01)

(52) U.S. Cl. ............... 514/278; 546/17; 546/18

(58) Field of Classification Search ............ 546/17, 546/18; 514/278
See application file for complete search history.

(56) References Cited

U.S. PATENT DOCUMENTS

| 5,908,830 A | 6/1999 | Smith et al. |
| 2002/0052371 A1 | 5/2002 | Fukami et al. |

FOREIGN PATENT DOCUMENTS

| WO | WO 01 13917 A | 3/2001 |
| WO | WO 01 70337 A | 9/2001 |
| WO | WO 02 06245 A | 1/2002 |

OTHER PUBLICATIONS

Shimada, et al., "Mice lacking melanin-concentrating hormone are hypophagic and lean" *Nature* 396:670-674(1998).
Borowsky, et al., "Antidepressant, anxiolytic and anorectic effects of a melanin-concentrating hormone-1 receptor antagonist" *Nature Medicine* 8:825-830(2002).
PCT International Search Report for PCT/US 03/20088 (CN01594K) Jun. 26, 2003—4 Pages.

*Primary Examiner*—Rita Desai
(74) *Attorney, Agent, or Firm*—William Y. Lee

(57) ABSTRACT

The present invention discloses compounds which, are novel antagonists for melanin-concentrating hormone (MCH), as well as methods for preparing such compounds. In another embodiment, the invention discloses pharmaceutical compositions comprising such MCH antagonists as well as methods of using them to treat obesity, metabolic disorders, eating disorders such as hyperphagia, and diabetes.

22 Claims, No Drawings

SPIROSUBSTITUTED PIPERIDINES AS SELECTIVE MELANIN CONCENTRATING HORMONE RECEPTOR ANTAGONISTS FOR THE TREATMENT OF OBESITY

CROSS REFERENCE TO RELATED APPLICATIONS

This application claims the benefit of U.S. Provisional Application 60/391,813 filed on Jun. 27, 2002.

FIELD OF THE INVENTION

This invention relates to antagonists for melanin-concentrating hormone (MCH) and their use in the treatment of metabolic and eating disorders. It generally discloses novel compounds having MCH receptor modulatory activity, pharmaceutical compositions containing one or more such modulators, methods of preparing such modulators and methods of using such modulators to treat obesity, diabetes and related disorders.

BACKGROUND OF THE INVENTION

MCH, a cyclic peptide, was first identified over a decade ago in teleost fish where it appears to regulate color change. More recently, MCH has been the subject of investigation for its possible role as a regulator of eating behavior in mammals. As reported by Shimada et al., *Nature*, Vol. 396 (17 Dec. 1998), pp. 670–673, MCH-deficient mice have reduced body weight and leanness due to hypophagia (reduced feeding). In view of their findings, it was suggested that antagonists of MCH may be effective for the treatment of obesity. U.S. Pat. No. 5,908,830 discloses a combination therapy for the treatment of diabetes or obesity involving the administration of a metabolic rate increasing agent and a feeding behavior modifying agent, an example of the latter being an MCH antagonist.

SUMMARY OF THE INVENTION

In one embodiment, this invention provides novel spiropiperidine compounds having MCH antagonist activity. These compounds are represented by structural formula I:

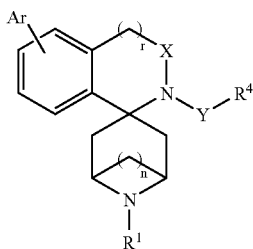

formula I or a pharmaceutically acceptable salt or solvate wherein

X is $-CH_2-$, $-SO_2-$, carbonyl, $-CHCH_3-$ or $-C(CH_3)_2-$;

Y is $-(CR^2R^3)_p C(O)NH-$, $-(CR^2R^3)_p NH-$, $-C(O)(CR^2R^3)_p NH-$, $-C(O)C(O)NH-$, $-C(O)(CR^2R^3)_p-$, $-C(CR^2R^3)_p-(CH=CH)_{p'}-$ or $-C(O)(CR^2R^3)_p-O-(CR^2R^3)_{p'}-$, wherein p is a number from 1 to 3 and when p is more than 1, each $(CR^2R^3)$ can be the same or different and p' is a number from 1 to 3 and when p' is more than 1, each $(CR^2R^3)$ can be the same or different;

n is 0, 2 or 3, and when n is 0, no connecting bond exists between the two carbons adjacent to the nitrogen;

r is a number from 0 to 1 and when r is 0, X is directly linked to the aromatic ring;

Ar is aryl, heteroaryl, $R^6$-substituted aryl or $R^6$-substituted heteroaryl;

$R^1$ is hydrogen, -alkyl, -cycloalkyl, aralkyl, heterocyclyl, heteroaralkyl, $-C(O)R^5$, $-C(O)OR^5$, $-C(O)NR^8R^9$, $-SO_2R^5$, $-SO_2NR^8R^9$, aryl, heteroaryl, $-CF_3$, -alkyl substituted with $R^{10}$, -cycloalkylalkyl, -cycloalkylalkyl substituted with $R^{10}$ on the cycloalkyl ring,

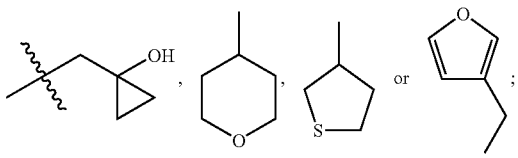

$R^2$ and $R^3$ can be the same or different, each being independently hydrogen or -alkyl; or $R^2$ and $R^3$ can be joined together with the carbon to which they are attached to form a 3 to 7-membered ring;

$R^4$ is aryl, heteroaryl, $R^7$-substituted aryl, $R^7$-substituted heteroaryl or $Y-R^4$ is

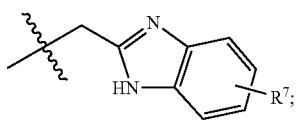

$R^5$ is -alkyl, aryl, aralkyl or heteroaryl;

$R^6$ is 1 to 5 substituents, each $R^6$ can be the same or different and each is independently selected from the group consisting of $-OH$, -alkoxy, $-OCF_3$, $-CN$, -alkyl, halogen, $-NR^8R^9$, $-C(O)NR^8R^9$, $-NR^8SO_2R^5$, $-SO_2NR^8R^9$, $-SO_2R^5$, $-C(O)R^5$, $-C(O)OR^5$, $-CF_3$, $-(CR^2R^3)_{p''}NR^8R^9$ where p" is a number from 1 to 3, $-CHO$, $-C=NOR^8$, $-NR^8C(O)R^5$, $-C(=NH)NR^8R^9$, $-C(=NCN)NR^8R^9$,

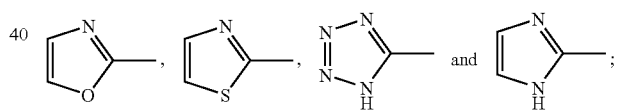

$R^7$ is hydrogen or 1 to 4 substituents, each $R^7$ can be the same or different and each is independently selected from the group consisting of, $-OH$, -alkoxy, $-OCF_3$, $-CN$, halogen, -nitro, $-NR^8R^9$, $-NR^8C(O)R^5$, $-C(O)NR^8R^9$, $-NR^8SO_2R^5$, $-SO_2NR^8R^9$, $-SO_2R^5$, $-C(O)R^5$, $-C(O)OR^8$, $-CF_3$, $-(CR^2R^3)_{p''}NR^8R^9$, $-(CR^2R^3)_{p''}NR^8C(O)R^5$ where p" is a number from 1 to 3, $-C(=NH)NR^8R^9$, $-C(=NCN)NR^8R^9$ and $-CHO$; or two adjacent $R^7$ groups can be joined together to form a methylenedioxy or ethylenedioxy group;

$R^8$ is hydrogen or -alkyl;

$R^9$ is hydrogen, -alkyl, aryl, substituted aryl, heteroaryl or aralkyl; and $R^{10}$ is $-OH$, -alkoxy, -cycloalkyl, $-C(O)NR^8R^9$, $-NR^8R^9$, $-NR^8SO_2R^5$, $-NR^8C(O)R^5$, $-NR^8C(O)OR^5$, $-NR^8C(O)NR^8R^9$, $-C(O)OH$ or $-C(O)OR^5$.

This invention is also directed to pharmaceutical compositions for the treatment of metabolic disorders such as obesity, and eating disorders such as hyperphagia. In one aspect, this invention is also directed to pharmaceutical compositions for the treatment of obesity which comprise an obesity treating amount of a compound of formula I, or a pharmaceutically acceptable salt or solvate of said compound and a pharmaceutically acceptable carrier.

DETAILED DESCRIPTION

The present invention relates to compounds that are represented by structural formula I, or a pharmaceutically acceptable salt or solvate, wherein the various moieties are as described above.

The compounds of formula I can be administered as racemic mixtures or enantiomerically pure compounds.

One group of preferred compounds are compounds of formula I wherein
X is —SO$_2$—;
Y is —C(R$^2$R$^3$)$_p$C(O)NH—;
R$^2$ and R$^3$ are hydrogen or alkyl;
n is 0;

and
r is 0.

An even further preferred group of compounds in the above preferred compounds are compounds wherein R$^2$ and R$^3$ are hydrogen.

Another group of preferred compounds are compounds of formula I wherein
X is carbonyl;
Y is —C(R$^2$R$^3$)$_p$C(O)NH—;
R$^2$ and R$^3$ are hydrogen or alkyl;
n is 0;

and
r is 0.

An even further preferred group of compounds are compounds in the above-preferred compounds wherein R$^2$ and R$^3$ are hydrogen.

Another preferred group of compounds are compounds of formula I wherein
X is —CH$_2$—;
Y is —C(R$^2$R$^3$)$_p$C(O)NH—;
R$^1$ is hydrogen, -alkyl, -cycloalkyl, heteroaralkyl, heterocyclyl, -alkyl substituted with -cycloalkyl, -cycloalkylalkyl, -alkyl substituted with R$^{10}$, —SO$_2$NR$^8$R$^9$, —SO$_2$R$^5$; —C(O)R$^5$ or —C(O)OR$^5$;
R$^2$ and R$^3$ are hydrogen or alkyl;
n is 0;
r is 1;

and
Ar is aryl or R$^6$-substituted aryl.

A further preferred compound in the above preferred compounds is a compound of formula I wherein
R$^1$ is hydrogen, methyl, ethyl, hydroxyethyl, cyclobutyl, cyclopentyl, cycloheptyl, -propyl, —SO$_2$CH$_3$, —SO$_2$N(CH$_3$)$_2$, —COCH$_3$, —C(O)OC(CH$_3$)$_3$, isopropyl, cyclopropylmethyl, heteroaryl,

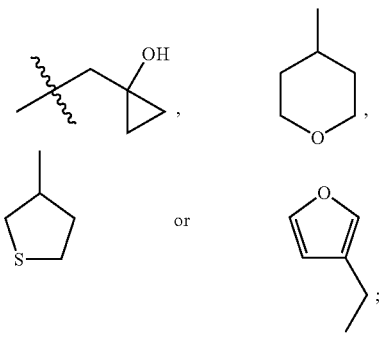

R$^2$ and R$^3$ are hydrogen;
Ar is R$^6$-substituted aryl;
R$^6$ is 1 to 5 substituents which can be the same or different and each is independently selected from the group consisting of halogen, —CF$_3$, —OCF$_3$, —CN, —CHO, —SO$_2$R$^5$, —C(O)OR$^8$, —C(O)R$^5$, —C(O)NR$^8$R$^9$ and

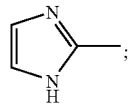

and
R$^7$ is two substituents which can be the same or different and independently selected from halogen, —CN and —CF$_3$.

A further preferred compound in the above preferred compounds is a compound of formula I wherein
R$^6$ numbers one;
R$^6$ is at the meta position of Ar;

and
R$^6$ is —CN, —C(=NH)NHaryl or —C(=NH)NH$_2$.

An even further group of preferred compounds are compounds of formula I wherein R$^7$ is selected from the group consisting of Cl, F and —CF$_3$, and R$^1$ is hydrogen, methyl, ethyl, hydroxyethyl, cyclobutyl, cyclopentyl, cycloheptyl, -propyl, —SO$_2$CH$_3$, —SO$_2$N(CH$_3$)$_2$, —COCH$_3$, —C(O)OC(CH$_3$)$_3$, isopropyl, cyclopropylmethyl, heteroaryl,

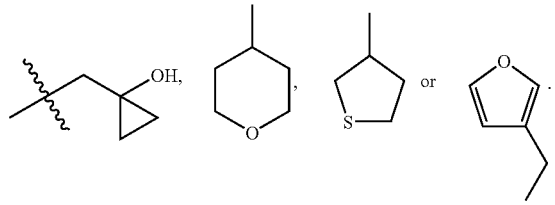

An even further preferred compound is a compound of formula I wherein
X is —CH$_2$—;
Y—R$^4$ is

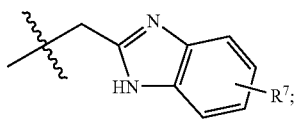

n is 0;
r is 1;
Ar is R$^6$-substituted aryl;
R$^1$ is alkyl or cyclopropylmethyl;
R$^6$ is —CN and is substituted at the meta position of Ar.

and
R$^7$ is hydrogen or halogen, or even more preferably, R$^7$ is chloride or fluoride.

Except where stated otherwise, the following definitions apply throughout the present specification and claims. These definitions apply regardless of whether a term is used by itself or in combination with other terms. Hence the definition of "alkyl" applies to "alkyl" as well as to the "alkyl" portions of "alkoxy", "alkylamino" etc.

As used above, and throughout the specification, the following terms, unless otherwise indicated, shall be understood to have the following meanings:

"Patient" includes both human and other animals.

"Mammal" means humans and other mammalian animals.

"Alkyl" means an aliphatic hydrocarbon group, which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means an alkyl group having about 1 to about 6 carbon atoms in the chain, which may be straight or branched. The term "substituted alkyl" means that the alkyl group may be substituted by one or more substituents which may be the same or different, each substituent being independently selected from the group consisting of halo, alkyl, aryl, -cycloalkyl, cyano, hydroxy, alkoxy, alkylthio, amino, —NH(alkyl), —NH(cycloalkyl), —N(alkyl)$_2$, carboxy and —C(O)O-alkyl. Non-limiting examples of suitable alkyl groups include methyl, ethyl, n-propyl, isopropyl, n-butyl, and t-butyl.

"Alkenyl" means an aliphatic hydrocarbon group comprising at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means an alkenyl group having about 2 to about 6 carbon atoms in the chain, which may be straight or branched. The term "substituted alkenyl" means that the alkenyl group may be substituted by one or more substituents which may be the same or different, each substituent being independently selected from the group consisting of halo, alkyl, aryl, -cycloalkyl, cyano, and alkoxy. Non-limiting examples of suitable alkenyl groups include ethenyl, propenyl, n-butenyl, and 3-methylbut-2-enyl.

"Alkynyl" means an aliphatic hydrocarbon group comprising at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means an alkynyl group having about 2 to about 6 carbon atoms in the chain, which may be straight or branched. Non-limiting examples of suitable alkynyl groups include ethynyl, propynyl and 2-butynyl. The term "substituted alkynyl" means that the alkynyl group may be substituted by one or more substituents which may be the same or different, each substituent being independently selected from the group consisting of alkyl, aryl and -cycloalkyl.

"Alkylene" means an alkanediyl group commonly having free valencies on two carbon atoms. Non-limiting examples include methylene, ethylene, propylene and the like.

"Aryl" means an aromatic monocyclic or multicyclic ring system comprising about 6 to about 14 carbon atoms, preferably about 6 to about 10 carbon atoms. The aryl group can be unsubstituted or substituted on the ring with one or more substituents which may be the same or different, each being independently selected from the group consisting of alkyl, aryl, —OCF$_3$, —OCOalkyl , —OCOaryl, —CF$_3$, heteroaryl, aralkyl, alkylaryl, heteroaralkyl, alkylheteroaryl, hydroxy, hydroxyalkyl, alkoxy, aryloxy, aralkoxy, acyl, aroyl, halo, haloalkyl, haloalkoxy, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, -cycloalkyl and heterocyclyl. Non-limiting examples of suitable aryl groups include phenyl and naphthyl. The "aryl" group can also be substituted by linking two adjacent carbons on its aromatic ring via a combination of one or more carbon atoms and one or more oxygen atoms such as, for example, methylenedioxy, ethylenedioxy, and the like.

"Arylene" means a bivalent group derived from an aromatic hydrocarbon by removal of a hydrogen atom from two ring carbon atoms. Non-limiting examples include phenylene and the like.

"Alkylenedioxy" means a combination of one or more carbon atoms and one or more oxygen atoms such as the following non-limiting examples that include methylenedioxy, ethylenedioxy, and the like.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted on the ring by replacing an available hydrogen on the ring by one or more substituents which may be the same or different, each being independently selected from the group consisting of alkyl, aryl, heteroaryl, aralkyl, alkylaryl, aralkenyl, heteroaralkyl, alkylheteroaryl, heteroaralkenyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, -cycloalkyl, cycloalkenyl and heterocyclyl. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, isoxazolyl, isothiazolyl, oxazolyl, thiazolyl, pyrrolyl, triazolyl, and the like.

"Heteroarylene" means a bivalent group derived from a heterocyclic aromatic compound by removal of a hydrogen atom from two ring carbon atoms such as, for example, the bivalent group derived from pyridine, pyrrole and the like.

"Aralkyl" means an aryl-alkyl- group in which the aryl and alkyl are as previously described. Preferred aralkyls comprise a lower alkyl group. Non-limiting examples of suitable aralkyl groups include benzyl, 2-phenethyl and a naphthlenylmethyl. The bond to the parent moiety is through the alkyl.

"Alkylaryl" means an alkyl-aryl- group in which the alkyl and aryl are as previously described. Preferred alkylaryls comprise a lower alkyl group. Non-limiting example of a suitable alkylaryl groups is tolyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted on the ring by replacing an available hydrogen on the ring by one or more substituents which may be the same or different, each being independently selected from the group consisting of alkyl, aryl, heteroaryl, aralkyl, alkylaryl, aralkenyl, heteroaralkyl, alkylheteroaryl, heteroaralkenyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl and heterocyclyl. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

"Cycloalkylalkyl" means a cycloalkyl-alkyl- group in which cycloalkyl and alkyl are as previously defined. Non-limiting examples of a suitable cycloalkylalkyl group includes cyclopropylmethyl. The bond to the parent moiety is through the alkyl.

"Halo" means fluoro, chloro, bromo or iodo groups. Preferred are fluoro, chloro or bromo, and more preferred are fluoro and chloro.

"Halogen" means fluorine, chlorine, bromine or iodine. Preferred are fluorine, chlorine or bromine, and more preferred are fluorine and chlorine.

"Haloalkyl" means an alkyl as defined above wherein one or more hydrogen atoms on the alkyl is replaced by a halo group defined above.

"Cycloalkenyl" means a non-aromatic mono or multicyclic ring system comprising about 3 to about 10 carbon atoms, preferably about 5 to about 10 carbon atoms which contains at least one carbon-carbon double bond. Preferred cycloalkenyl rings contain about 5 to about 7 ring atoms. The cycloalkenyl can be optionally substituted on the ring by replacing an available hydrogen on the ring by one or more substituents which may be the same or different, each being independently selected from the group consisting of alkyl, aryl, heteroaryl, aralkyl, alkylaryl, aralkenyl, heteroaralkyl, alkylheteroaryl, heteroaralkenyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl and heterocyclyl. Non-limiting examples of suitable monocyclic cycloalkenyls include cyclopentenyl, cyclohexenyl, cycloheptenyl, and the like. Non-limiting example of a suitable multicyclic cycloalkenyl is norbornylenyl.

"Heterocyclyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. The heterocyclyl can be optionally substituted on the ring by replacing an available hydrogen on the ring by one or more substituents which may be the same or different, each being independently selected from the group consisting of alkyl, aryl, heteroaryl, aralkyl, alkylaryl, aralkenyl, heteroaralkyl, alkylheteroaryl, heteroaralkenyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl and heterocyclyl. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, pyranyl, tetrahydrothiophenyl, morpholinyl and the like.

"Arylcycloalkenyl" means a group derived from a fused aryl and cycloalkenyl as defined herein by removal of a hydrogen atom from the cycloalkenyl portion. Preferred arylcycloalkenyls are those wherein aryl is phenyl and the cycloalkenyl consists of about 5 to about 6 ring atoms. The arylcycloalkenyl can be optionally substituted on the ring by replacing an available hydrogen on the ring by one or more substituents which may be the same or different, each being independently selected from the group consisting of alkyl, aryl, heteroaryl, aralkyl, alkylaryl, aralkenyl, heteroaralkyl, alkylheteroaryl, heteroaralkenyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl and heterocyclyl. Non-limiting examples of suitable arylcycloalkenyls include 1,2-dihydronaphthalene, indene, and the like. The bond to the parent moiety is through a non-aromatic carbon atom.

"Aralkenyl" means an aryl-alkenyl- group in which the aryl and alkenyl are as previously described. Preferred aralkenyls contain a lower alkenyl group. Non-limiting examples of suitable aralkenyl groups include 2-phenethenyl and 2-naphthylethenyl. The bond to the parent moiety is through the alkenyl.

"Heteroaralkyl" means a heteroaryl-alkyl- group in which the heteroaryl and alkyl are as previously described. Preferred heteroaralkyls contain a lower alkyl group. Non-limiting examples of suitable aralkyl groups include pyridylmethyl, 2-(furan-3-yl)ethyl and quinolin-3-ylmethyl. The bond to the parent moiety is through the alkyl.

"Heteroaralkenyl" means an heteroaryl-alkenyl-group in which the heteroaryl and alkenyl are as previously described. Preferred heteroaralkenyls contain a lower alkenyl group. Non-limiting examples of suitable heteroaralkenyl groups include 2-(pyrid-3-yl)ethenyl and 2-(quinolin-3-yl)ethenyl. The bond to the parent moiety is through the alkenyl.

"Alkoxyalkyl" means an alkoxy-alkyl- group in which alkyl and alkoxy are as previously defined. Non-limiting examples of suitable alkoxyalkyl groups include methoxymethyl, ethoxymethyl, methoxyethyl and ethoxyethyl.

"Aryloxyalkyl" means an aryloxy-alkyl-group in which aryl and alkoxy are as previously defined. Non-limiting examples of suitable aryloxyalkyl groups include benzoxymethyl, substituted aryloxymethyl, benzoxyethyl and substituted aryloxyethyl.

"Hydroxyalkyl" means a HO-alkyl- group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)—, alkenyl-C(O)—, Alkynyl-C(O)—, cycloalkyl-C(O)—, cycloalkenyl-C(O)—, or cycloalkynyl-C(O)— group in which the various groups are as previously described. The bond to the parent moiety is through the carbonyl. Preferred acyls contain a lower alkyl. Non-limiting examples of suitable acyl groups include formyl, acetyl, propanoyl, 2-methylpropanoyl, and cyclohexanoyl.

"Aroyl" means an aryl-C(O)— group in which the aryl group is as previously described. The bond to the parent moiety is through the carbonyl. Non-limiting examples of suitable groups include benzoyl and 1- and 2-naphthoyl.

"Alkoxy" means an alkyl-O— group in which the alkyl group is as previously described. Non-limiting examples of suitable alkoxy groups include methoxy, ethoxy, n-propoxy and isopropoxy. The alkyl group is linked to an adjacent moiety through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Alkylamino" means an —NH$_2$ or —NH$_3^+$ group in which one or more of the hydrogen atoms on the nitrogen is replaced by an alkyl group as defined above.

"Alkylthio" means an alkyl-S— group in which the alkyl group is as previously described. Non-limiting examples of suitable alkylthio groups include methylthio, ethylthio, i-propylthio and heptylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkoxy group defined earlier linked to an adjacent moiety through a carbonyl. Non-limiting examples of alkoxycarbonyl groups include —C(O)—CH$_3$, —C(O)—CH$_2$CH$_3$ and the like.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-S(O$_2$)— group. Preferred groups are those in which the alkyl group is lower alkyl. The bond to the parent moiety is through the sulfonyl.

"Alkylsulfinyl" means an alkyl-S(O)— group. Preferred groups are those in which the alkyl group is lower alkyl. The bond to the parent moiety is through the sulfinyl.

"Arylsulfonyl" means an aryl-S(O$_2$)— group. The bond to the parent moiety is through the sulfonyl.

"Arylsulfinyl" means an aryl-S(O)— group. The bond to the parent moiety is through the sulfinyl.

The term "optionally substituted" means optional substitution with the specified groups, radicals or moieties.

As used herein, the term "composition" is intended to encompass a product comprising the specified ingredients in the specified amounts, as well as any product which results, directly or indirectly, from combination of the specified ingredients in the specified amounts.

Solvates of the compounds of the invention are also contemplated herein. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is H$_2$O.

"Effective amount" or "therapeutically effective amount" is meant to describe an amount of compound of the present invention effective to treat a patient (e.g., human) having a disease or condition mediated by MCH, and thus producing the desired therapeutic effect.

The compound of formula I forms salts which are also within the scope of this invention. Reference to a compound of formula I, herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compound of the formula I may be formed, for example, by reacting a compound of formula I with an amount of acid or base, such as an equivalent amount, in a medium such as one in which the salt precipitates or in an aqueous medium followed by lyophilization.

Exemplary acid addition salts include acetates, adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, 2-naphthalenesulfonates, nicotinates, nitrates, oxalates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates,) undecanoates, and the like. Additionally, acids which are generally considered suitable for the formation of pharmaceutically useful salts from basic pharmaceutical compounds are discussed, for example, by S. Berge et al, *Journal of Pharmaceutical Sciences* (1977) 66(1) 1–19; P. Gould, *International J. of Pharmaceutics* (1986) 33 201–217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine and the like. Basic nitrogen-containing groups may be quarternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Compounds of formula I, and salts and solvates thereof, may exist in their tautomeric form (for example, as an amide or imino ether). All such tautomeric forms are contemplated herein as part of the present invention.

All stereoisomers (for example, geometric isomers, optical isomers and the like) of the present compounds (including those of the salts and solvates of the compounds), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate" and the like, is intended to equally apply to the salt and solvate of enantiomers, stereoisomers, rotamers, tautomers or racemates of the inventive compounds.

When any variable (e.g., aryl, heterocycle, $R^2$, etc.) occurs more than one time in any constituent or in formula I, its definition on each occurrence is independent of its definition at every other occurrence. Also, combinations of substituents and/or variables are permissible only if such combinations result in stable compounds.

Spiropiperidines of formula I are highly selective, high affinity Melanin Concentrating Hormone (MCH) receptor antagonists useful for the treatment of obesity.

A preferred group of compounds are those as follows: 7a, 7b, 7c, 7d, 7e, 8a, 8b, 8c, 8d, 8e, 8f, 8g, 8h, 8i, 10c, 11a, 11b, 11c, 11d, 11e, 11f, 11g, 11h, 11i, 11j, 12a, 12d, 12e, 12f, 30a, 30b, 30c and 30d.

Another aspect of this invention is a method of treating a patient (e.g., human) having a disease or condition mediated by MCH by administering a therapeutically effective amount of at least one compound of formula I, or a pharmaceutically acceptable salt or solvate of said compound to the patient.

A preferred dosage is about 0.001 to 100 mg/kg/day of the compound of formula I. An especially preferred dosage is about 0.01 to 25 mg/kg/day of a compound of formula I, or a pharmaceutically acceptable salt or solvate of said compound.

Another aspect of this invention is directed to a method of treating obesity comprising administering to a patient in need of such treatment a therapeutically effective amount of at least one compound of formula I, or a pharmaceutically acceptable salt or solvate of said compound.

Another aspect of this invention is directed to a method for treating eating and metabolic disorders such as bulimia and anorexia comprising administering to a patient a therapeutically effective amount of at least one compound of formula I, or a pharmaceutically acceptable salt or solvate of said compound.

Another aspect of this invention is directed to a method for treating hyperlipidemia comprising administering to a patient a therapeutically effective amount of at least one compound of formula I, or a pharmaceutically acceptable salt or solvate of said compound.

Another aspect of this invention is directed to a method for treating cellulite and fat accumulation comprising administering to a patient a therapeutically effective amount of at least one compound of formula I, or a pharmaceutically acceptable salt or solvate of said compound.

Another aspect of this invention is directed to a method for treating type II diabetes comprising administering to a patient a therapeutically effective amount of at least one compound of formula I, or a pharmaceutically acceptable salt or solvate of said compound.

In addition to the "direct" effect of the compounds of this invention on the MCH subtype, there are diseases and conditions that will benefit from the weight loss such as insulin resistance, impaired glucose tolerance, Type II Diabetes, hypertension, hyperlipidemia, cardiovascular disease, gall stones, certain cancers, and sleep apnea.

This invention is also directed to pharmaceutical compositions, which comprise at least one compound of formula I, or a pharmaceutically acceptable salt or solvate of said compound and at least one pharmaceutically acceptable carrier.

This invention is also directed to pharmaceutical compositions for the treatment of obesity which comprise an obesity treating amount of at least one compound of formula I, or a pharmaceutically acceptable salt or solvate of said compound and at least one pharmaceutically acceptable carrier.

Compounds of formula I, can be produced by processes known to those skilled in the art using either solution phase or solid phase synthesis as shown in the following reaction schemes, in the preparations and examples below, and by using the methods described in WO 98/05292, the disclosure of which is incorporated herein by reference.

The synthesis of structures of formula I, wherein n is 0, r is 0, X is —$CH_2$—, and Y is —$CH_2C(O)NH$— is illustrated below in Scheme 1:

Scheme 1

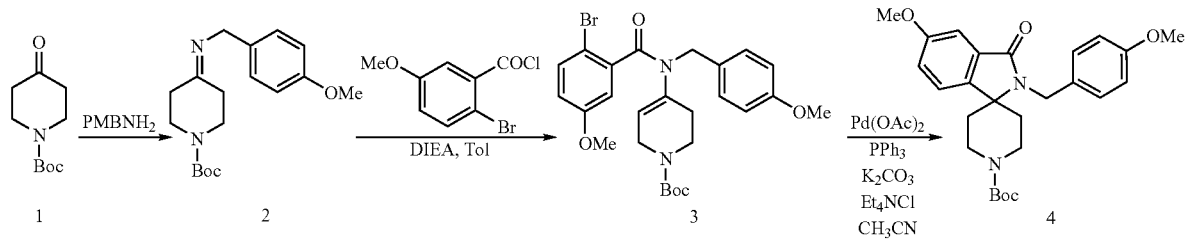

1. TFA/DCM
2. $NaBH(OAc)_3$/DCE/HOAc

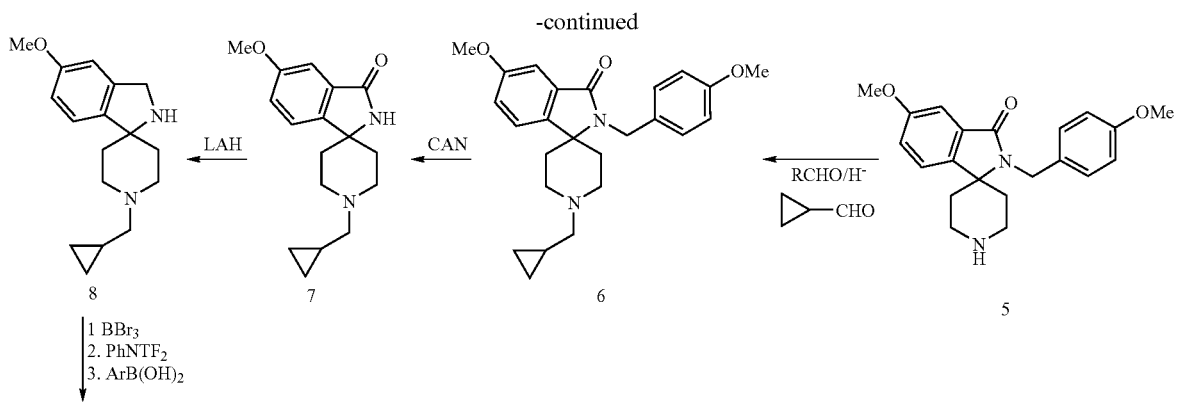
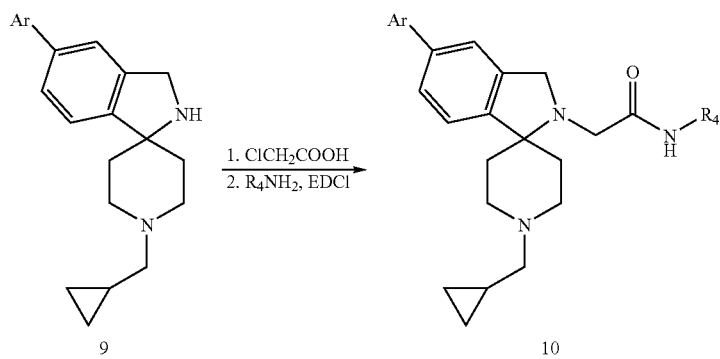
The initial cyclization is described in WO 0114316.
Oxidized analogs of the compounds of formula I wherein n is 0, r is 0, x is carbonyl and Y is —CH$_2$C(O)NH— by the method described in scheme 2:
Scheme 2
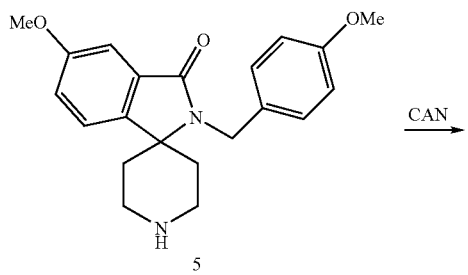
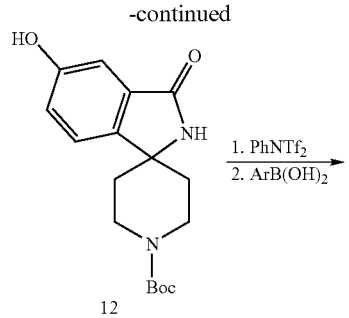
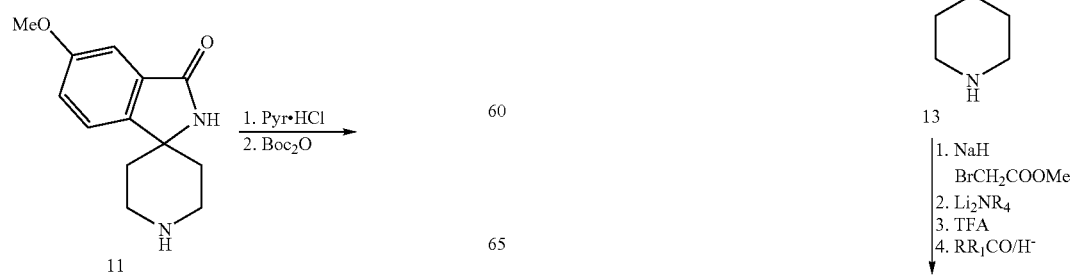

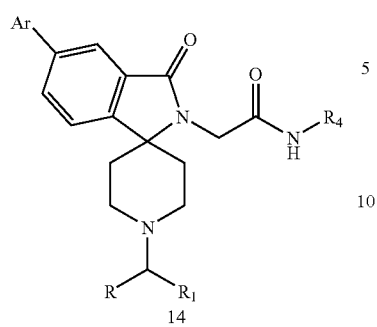
Compounds of formula I wherein n is 0, r is 1, X is —CH$_2$— and Y is —(CH$_2$)$_p$C(O)NH— are prepared according to the method described in scheme 3:
Scheme 3
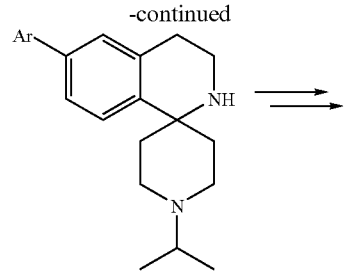
The synthesis of analogs of formula I wherein n is 0, r is 0, X is —SO$_2$— and Y is —(CH$_2$)$_p$C(O)NH— is illustrated below in Scheme 4:
Scheme 4

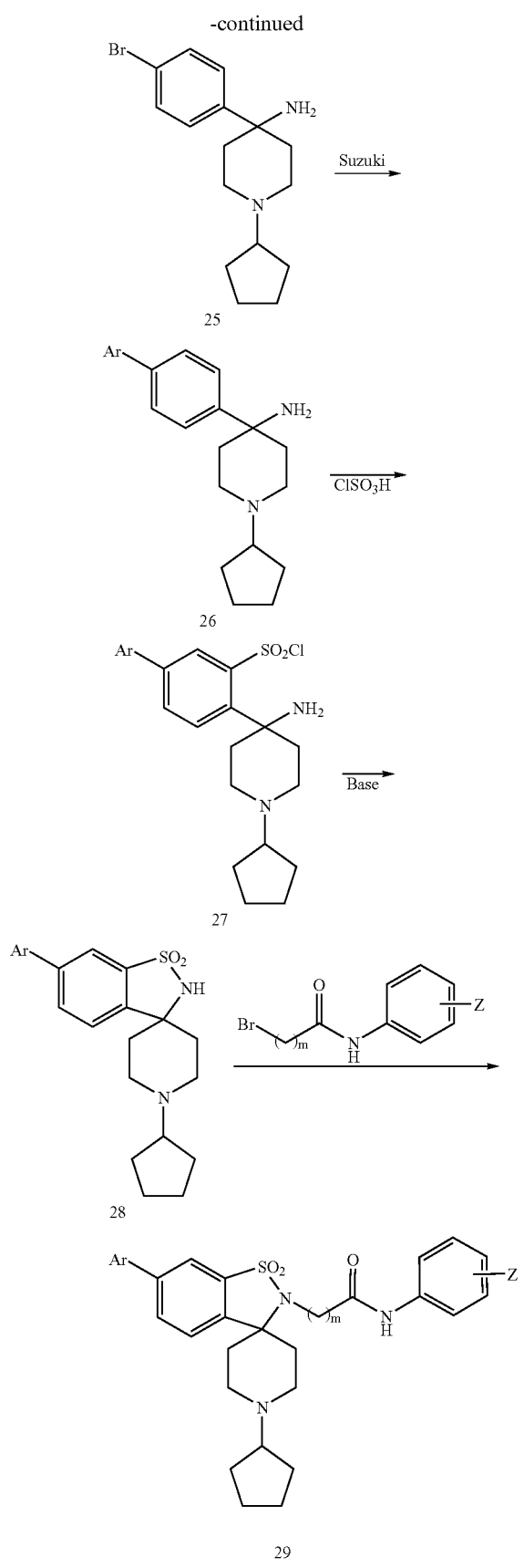

Combinatorial libraries of compounds of formula I can also be prepared using solid phase chemistry as shown in the schemes above.

Alternative mechanistic pathways and analogous structures within the scope of the invention would be apparent to those skilled in the art.

Starting materials are prepared by known methods and/or methods described in the Preparations.

The compounds of formula I exhibit MCH receptor antagonizing activity, which has been correlated with pharmaceutical activity for treating an eating disorder, such as obesity and hyperphagia, and diabetes.

The compounds of formula I display pharmacological activity in a test procedure designed to demonstrate MCH receptor antagonist activity. The compounds are non-toxic at pharmaceutically therapeutic doses.

Yet another aspect of this invention is combinations of a compound of formula I, or a pharmaceutically acceptable salt or solvate of said compound and other compounds as described below.

Accordingly, another aspect of this invention is a method for treating obesity comprising administering to a patient (e.g., a female or male human)

a. an amount of a first compound, said first compound being a compound of formula I, or a pharmaceutically acceptable salt or solvate of said compound; and b. an amount of a second compound, said second compound being an antiobesity and/or anorectic agent such as a $\beta_3$ agonist, a thyromimetic agent, an anoretic agent, or an NPY antagonist wherein the amounts of the first and second compounds result in a therapeutic effect.

This invention is also directed to a pharmaceutical combination composition comprising: a therapeutically effective amount of a composition comprising a first compound, said first compound being a compound of formula I, or a pharmaceutically acceptable salt or solvate of said compound a second compound, said second compound being an antiobesity and/or anorectic agent such as a $\beta_3$ agonist, a thyromimetic agent, an anoretic, or an NPY antagonist; and/or optionally a pharmaceutical carrier, vehicle or diluent.

Another aspect of this invention is a kit comprising:

a. an amount of a compound of formula I, or a pharmaceutically acceptable salt or solvate of said compound and a pharmaceutically acceptable carrier, vehicle or diluent in a first unit dosage form;

b. an amount of an antiobesity and/or anorectic agent such as a $\beta_3$ agonist, a thyromimetic agent, an anoretic agent, or an NPY antagonist and a pharmaceutically acceptable carrier, vehicle or diluent in a second unit dosage form; and c. means for containing said first and second dosage forms wherein the amounts of the first and second compounds result in a therapeutic effect.

Preferred antiobesity and/or anorectic agents (taken singly or in any combination thereof) in the above combination methods, combination compositions and combination kits are:

phenylpropanolamine, ephedrine, pseudoephedrine, phentermine, a cholecystokinin-A (hereinafter referred to as CCK-A) agonist, a monoamine reuptake inhibitor (such as sibutramine), a sympathomimetic agent, a serotonergic agent (such as dexfenfluramine or fenfluramine), a dopamine agonist (such as bromocriptine), a melanocyte-stimulating hormone receptor agonist or mimetic, a melanocyte-stimulating hormone analog, a cannabinoid receptor antagonist, a melanin concentrating hormone antagonist, the OB protein (hereinafter referred to as "leptin"), a leptin analog, a leptin receptor agonist, a galanin antagonist or a GI lipase inhibitor or decreaser (such as orlistat). Other anorectic agents include bombesin agonists, dehydroepiandrosterone or analogs thereof, glucocorticoid receptor agonists and antagonists, orexin receptor antagonists, urocortin binding protein antagonists, agonists of the glucagon-like peptide-1 receptor such as Exendin and ciliary neurotrophic factors such as Axokine.

Another aspect of this invention is a method treating diabetes, comprising administering to a patient (e.g., a female or male human).

a. an amount of a first compound, said first compound being a compound of formula I, or a pharmaceutically acceptable salt or solvate of said compound; and b. an amount of a second compound, said second compound being an aldose reductase inhibitor, a glycogen phosphorylase inhibitor, a sorbitol dehydrogenase inhibitor, a protein tyrosine phosphatase 1B inhibitor, a dipeptidyl protease inhibitor, insulin (including orally bioavailable insulin preparations), an insulin mimetic, metformin, acarbose, a PPAR-gamma ligand such as troglitazone, rosaglitazone, pioglitazone or GW-1929, a sulfonylurea, glipazide, glyburide, or chlorpropamide wherein the amounts of the first and second compounds result in a therapeutic effect.

This invention is also directed to a pharmaceutical combination composition comprising: a therapeutically effective amount of a composition comprising a first compound, said first compound being a compound of formula I, or a pharmaceutically acceptable salt or solvate of said compound;

a second compound, said second compound being an aldose reductase inhibitor, a glycogen phosphorylase inhibitor, a sorbitol dehydrogenase inhibitor, a protein tyrosine phosphatase 1B inhibitor, a dipeptidyl protease inhibitor, insulin (including orally bioavailable insulin preparations), an insulin mimetic, metformin, acarbose, a PPAR-gamma ligand such as troglitazone, rosaglitazone, pioglitazone, or GW-1929, a sulfonylurea, glipazide, glyburide, or chlorpropamide; and optionally a pharmaceutical carrier, vehicle or diluent.

Another aspect of this invention is a kit comprising:

a. an amount of a compound of formula I, or a pharmaceutically acceptable salt or solvate of said compound and a pharmaceutically acceptable carrier, vehicle or diluent in a first unit dosage form;

b. an amount of an aldose reductase inhibitor, a glycogen phosphorylase inhibitor, a sorbitol dehydrogenase inhibitor, a protein tyrosine phosphatase 1B inhibitor, a dipeptidyl protease inhibitor, insulin (including orally bioavailable insulin preparations), an insulin mimetic, metformin, acarbose, a PPAR-gamma ligand such as troglitazone, rosaglitazone, pioglitazone, or GW-1929, a sulfonylurea, glipazide, glyburide, or chlorpropamide and a pharmaceutically acceptable carrier, vehicle or diluent in a second unit dosage form; and c. means for containing said first and second dosage forms wherein the amounts of the first and second compounds result in a therapeutic effect.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences*, 18th Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

The compounds of this invention may also be delivered subcutaneously.

Preferably the compound is administered orally.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 1 mg to about 100 mg, preferably from about 1 mg to about 50 mg, more preferably from about 1 mg to about 25 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 300 mg/day, preferably 1 mg/day to 50 mg/day, in two to four divided doses.

The invention disclosed herein is exemplified by the following preparations and examples that should not be construed to limit the scope of the disclosure. Alternative mechanistic pathways and analogous structures will be apparent to those skilled in the art.

Where NMR data are presented, $^1$H spectra were obtained on either a Varian VXR-200 (200 MHz, $^1$H), Varian Gemini-300 (300 MHz) or XL-400 (400 MHz) and are reported as ppm down field from Me$_4$Si with number of protons, multiplicities, and coupling constants in Hertz indicated parenthetically. Where LC/MS data are presented, analyses was performed using an Applied Biosystems API-100 mass spectrometer and Shimadzu SCL-10A LC column: Altech platinum C18, 3 micron, 33 mm×7 mm ID; gradient flow: 0 min—10% CH$_3$CN, 5 min—95% CH$_3$CN, 7 min—95% CH$_3$CN, 7.5 min—10% CH$_3$CN, 9 min—stop. The retention time and observed parent ion are given.

The following solvents and reagents may be referred to by their abbreviations in parenthesis:

Thin layer chromatography (TLC);
dichloromethane (DCM or $CH_2Cl_2$);
ethyl acetate (AcOEt or EtOAc);
methanol (MeOH);
acetonitrile ($CH_3CN$);
N,N-dimethylformamide (DMF);
triethylamine ($Et_3N$ or TEA);
butoxycarbony (n-Boc or Boc);
boron tribromide ($BBr_3$);
sodium iodide (NaI);
High Performance Liquid Chromatography (HPLC);
melting point (M.pt.);
nuclear magnetic resonance spectroscopy (NMR);
mass spectral analysis (MS);
milliliters (mL);
grams (g);
room temperature (ambient) about 25° C. (rt).

EXAMPLES

Spirocyclic Tetrahydroisoquinolines: Synthesis of Compounds of Formula I

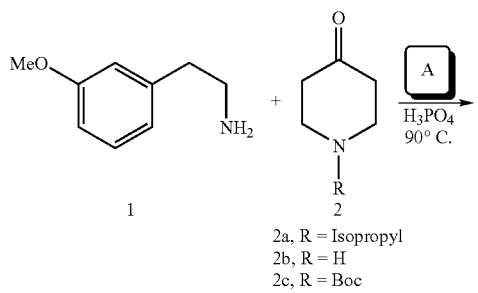

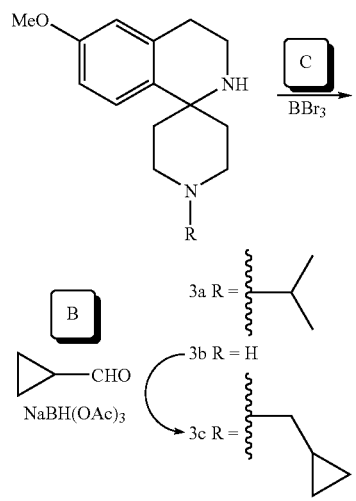

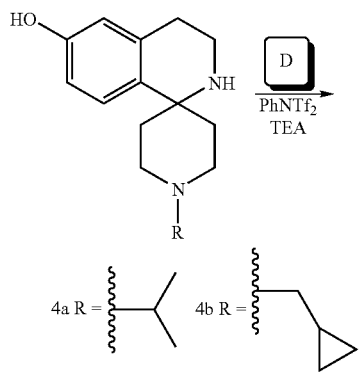

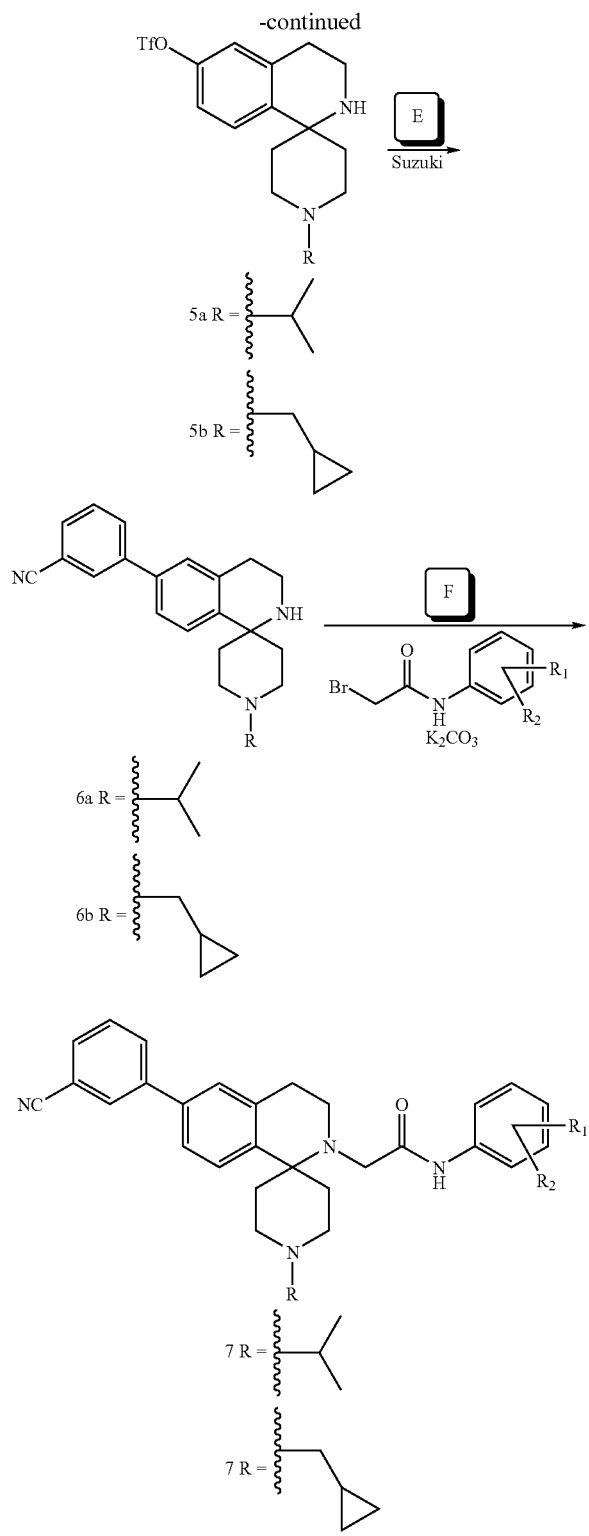

Experimental Procedures:

Procedure A: 3-Methoxyphenethyl amine 1 (15 g, 0.099 mol) was dissolved in 100 mL of 85% phosphoric acid and N-isopropyl piperidone 2a (14.1 g, 0.10 mol) was added slowly at room temperature. The resulting mixture was heated at 90° C. for 12 h. The reaction mixture was cooled and poured into ice water, neutralized with aq. sodium hydroxide solution and extracted with EtOAc and $CH_2Cl_2$. The combined organic layers were washed with brine and dried over sodium sulfate. The solvent was removed in vacuo and the product was isolated by $SiO_2$ chromatography using 20–30% methanol/dichloromethane as eluent to afford 20.4 g of compound 3a as viscous oil: $^1$HNMR (CDCl$_3$) δ: 7.28 (s, 1H), 6.74 (s, 1H), 6.57 (s, 1H), 3.76 (s, 3H), 3.04 (m, 2H), 2.71 (m, 4H), 2.52 (m, 2H), 2.05 (m, 2H), 1.70 (m, 2H), 1.09 (d, 6H).

Compound 3b was synthesized analogously starting with N-Boc piperidone 2c to afford compound 3b as viscous oil. $^1$HNMR (CDCl$_3$) δ: 7.2 (d, 1H), 6.7 (d, 1H), 6.54 (s, 1H), 3.73 (s, 3H), 3.0 (m, 4H), 2.84 (m, 2H), 2.67 (m, 2H), 1.94 (m, 2H), 1.64 (m, 2H).

Procedure B: Compound 3b (2.6 g, 0.011 mol) was mixed with cyclopropane carboxaldehyde (0.96 g, 0.013 mol) and triacetoxy sodium borohydride (4.91 g, 2 eq) in dichloromethane (20 mL) and stirred at room temperature overnight. The reaction was quenched by the addition of saturated sodium bicarbonate solution and the aqueous layer was extracted with dichloromethane. The organic layer was washed with brine and dried over sodium sulfate. The solvent was removed in vacuo and the product was isolated by SiO$_2$ chromatography using 3–5% methanol in dichloromethane as eluent to afford 1.5 g of compound 3c as oil: $^1$HNMR (CDCl$_3$) δ: 7.19 (d, 1H), 6.65 (d, 1H), 6.5 (s, 1H), 3.72 (3H), 3.2 (m, 2H), 2.93 (m, 4H), 2.66 (m, 4H), 2.3 (m, 2H), 1.67 (m, 2H), 1.1 (m, 1H), 0.65 (m, 2H), 0.27 (m, 2H).

Procedure C: To a solution of compound 3a (5.5 g, 0.02 mol) in 100 mL of dichloromethane at −78° C. was added 6 mL of BBr$_3$ (0.063 mol, 3 eq) and the reaction was stirred at that temperature for 30 minutes. The reaction mixture was warmed to room temperature and stirred for 3 hours. The reaction mixture was cooled to −78° C., quenched with 50 mL of MeOH, and warmed to room temperature. The mixture was then heated under reflux for 30 minutes. The solvent was removed in vacuo and the product was crystallized from methanol to give 4.5 g of compound 4a as a colorless solid: $^1$HNMR (CDCl$_3$) δ: 7.42 (d, 1H), 6.8 (d, 1H), 6.63 (s, 1H), 3.72–3.55 (m, 7H), 3.12 (m, 2H), 2.92 (m, 2H), 2.47 (d, 2H), 1.5 (d, 6H).

Compound 4b was synthesized analogously starting with tetrahydroisoquinoline 3c to afford compound 4b as colorless solid: $^1$HNMR (CDCl$_3$) δ: 6.96 (d, 1H), 6.58 (q,1H), 6.46 (d, 1H), 2.94–3.03 (m, 4H), 2.50–2.63 (m, 4H), 2.42 (d, 2H), 2.18 (m, 2H), 1.68 (d, 2H), 0.95 (m, 1H), 0.54 (m, 2H), 0.16 (m, 2H).

Procedure D: The phenol (4.5 g, 0.017 mol) was suspended in 500 mL of dichloromethane. Triethylamine (20 mL) was added to generate a clear solution. This solution was cooled to −78° C., treated with 12.36 g of N-phenyl triflimide (2 eq.) and stirred for 1 h. The reaction mixture was warmed to room temperature and an additional 6 g of N-phenyl triflimide was added. The reaction was stirred at room temperature for 3 hours and water (100 mL) was added. The reaction mixture was extracted with dichloromethane and washed sequentially with sodium bicarbonate solution and brine. The organic layer was dried over sodium sulfate and the solvent was removed in vacuo. The triflate 5a was passed through a short SiO$_2$ column using 3–5% methanol/dichloromethane as eluent and used directly in the next step.

Compound 5b was synthesized analogously starting with phenol 4b and used directly in the next step.

Procedure E: The triflate 5a was dissolved in toluene/methanol (100 mL, 1:1) and treated with 3-cyanophenyl boronic acid (6 g, 0.041 mol, 2.2 eq) and sodium carbonate solution (2M aq. solution, 20 mL). The contents were degassed for 10 minutes with nitrogen and treated with tetrakistriphenylphosphine palladium (1.0 g, 5 mol %). The contents were heated at 90° C. overnight. The solid particles were filtered through a small pad of celite and washed with ethyl acetate (EtOAc). The solvent was removed in vacuo and the product was isolated by SiO$_2$ chromatography using 3–10% methanol/dichloromethane as eluent to give 3.0 g of compound 6a as a light brown solid: $^1$HNMR (CDCl$_3$) δ: 7.69 (m, 2H), 7.50 (m, 3H), 7.26 (m, 2H), 3.49 (m, 4), 3.23 (s, 2H), 3.03 (s, 2H), 2.79 (s, 2H), 2.59 (m, 2H), 1.96 (d, 2H), 1.41 (d, 6H).

Compound 6b was synthesized analogously starting with triflate 5b to afford compound 6b as a light brown solid: $^1$HNMR (CDCl$_3$) δ: 7.8–7.33 (m, 7H), 3.04 (m, 2H), 2.92 (m, 2H), 2.79 (m, 2H), 2.32 (m, 4H), 2.2 (m, 2H), 1.72 (d, 2H), 1.3 (s, 1H), 0.9 (m, 1H), 0.49 (m, 2H), 0.08 (m, 2H).

PROCEDURE F: Compound 6a (0.05 g, 0.14 mmol) was dissolved in DMF (5 mL) and treated with the alkylating agent (0.1 g, 2.2 eq), K$_2$CO$_3$ (0.1 g, 5 eq) and NaI (0.1 g, 4.5 eq). The contents were heated in a sealed tube at 150° C. for 4 hours. The solvent was removed in vacuo and the residue was purified by prep SiO$_2$ TLC eluting with 5% methanol/dichloromethane to give 0.03 g of compound 7a as a light brown solid: ES MS: calcd for C$_{32}$H$_{33}$Cl$_2$N$_4$O$^+$ m/z=546.20; found m/z=547.1 (M+1)$^+$.

The following compounds can be prepared by an analogous procedure starting from compound 6a or from compound 6b.

| Cpd.# | STRUCTURE | Analytical Data |
|---|---|---|
| 7a | 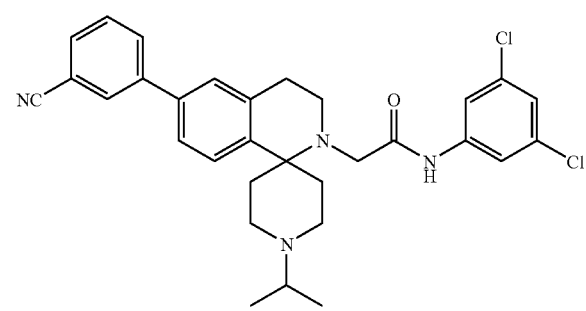 | ES MS: calcd for C$_{32}$H$_{33}$Cl$_2$N$_4$O+ m/z = 546.20; found m/z = 547.1 (M + 1)$^+$ |

| Cpd.# | STRUCTURE | Analytical Data |
|---|---|---|
| 7b | 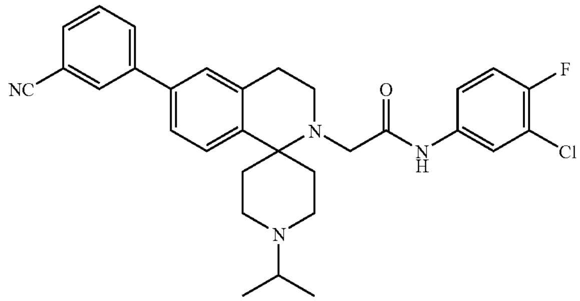 | ES MS: calcd for $C_{32}H_{33}ClFN_4O^+$ m/z = 530.22; found m/z = 531.1 $(M + 1)^+$ |
| 7c | 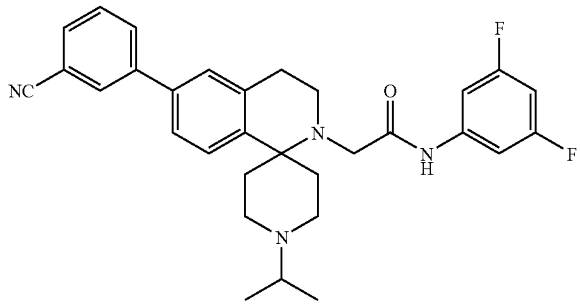 | ES MS: calcd for $C_{32}H_{33}F_2N_4O^+$ m/z = 514.25; found m/z = 515.1 $(M + 1)^+$ |
| 7d | 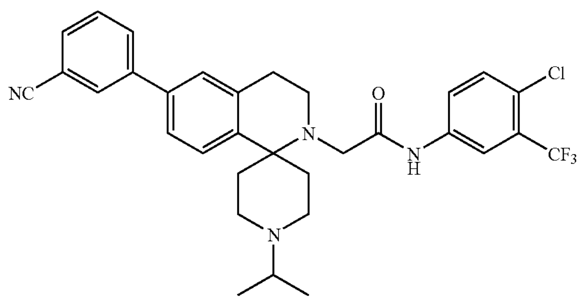 | ES MS: calcd for $C_{32}H_{33}ClF_3N_4O^+$ m/z = 580.22; found m/z = 581.1 $(M + 1)^+$ |
| 7e | 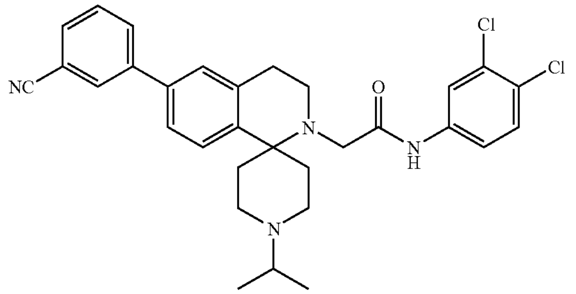 | ES MS: calcd for $C_{31}H_{33}Cl_2N_4O^+$ m/z = 546.20; found m/z = 547.1 $(M + 1)^+$ |
| 8a | 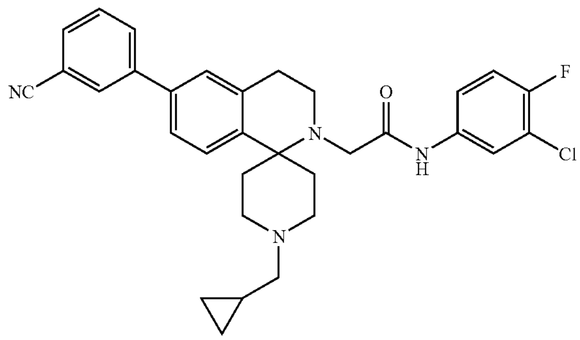 | ES MS: calcd for $C_{32}H_{33}ClFN_4O$ m/z = 543.23; found m/z = 543.1 $(M + 1)^+$ |

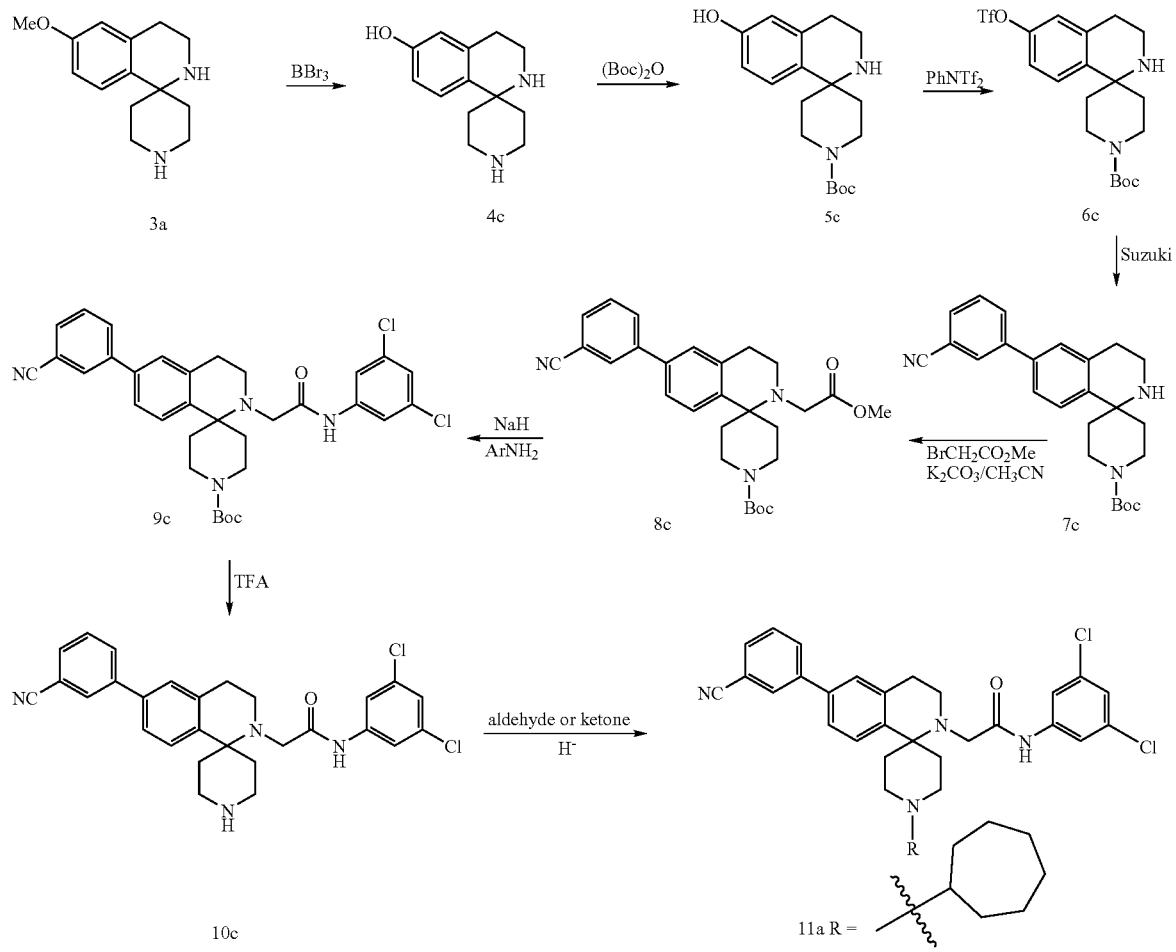

Compound 4c: To a solution of compound 3a (7.3 g, 0.031 mol) in 40 mL of dichloromethane at −78° C. was added 104 mL of BBr$_3$ (1 M solution in DCM, 0.104 mol, 3.3 eq) and the reaction was stirred at that temperature for 30 minutes. The reaction mixture was warmed to room temperature and stirred overnight. The reaction mixture was cooled to 0° C. and quenched with 50 mL MeOH and warmed to room temperature. The mixture was then heated under reflux for 30 minutes. The solvent was removed in vaccuo and the product was isolated by SiO$_2$ chromatography using 20% methanol/dichloromethane as eluent to give 4c as a light brown solid: ES MS: calcd for $C_{13}H_{19}N_2O^+$ m/z=219.15; found m/z=219.1 (M+1)$^+$.

Compound 5c: The phenol (10.9 g, 0.05 mol) was suspended in methanol (100 mL) and treated with boc anhydride (12.0 g, 1.1 eq). The reaction mixture was stirred over the weekend and the solvent was removed in vacuo. The solvent was removed in vaccuo and the product was isolated by SiO$_2$ chromatography using 10% methanol/dichloromethane as eluent to give 5.82 g of 5c as a colorless solid. ES MS: calcd for $C_{18}H_{27}N_2O^+$ m/z=319.20; found m/z=319.1 (M+1)$^+$.

Compound 6c: The phenol (5.7 g, 0.018 mol) was suspended in 200 mL of dichloromethane. 70 mL of triethylamine was added to get a clear solution. This solution was cooled to −78° C. and treated with N-phenyl triflimide (12.8 g, 2 eq.) and stirred for 1 h. The reaction mixture was warmed to room temperature and stirred for 3 hours. 100 mL of water was added to the reaction mixture. Extracted with dichloromethane and the organic layer was washed with sodium bicarbonate solution and brine. It was dried over sodium sulfate and the solvent was removed in vaccuo. The resulting triflate was isolated by a short SiO$_2$ column using 80% ethylacetate/hexane as eluent. ES MS: calcd for $C_{19}H_{26}F_3N_2O_5^+$ m/z=451.15; found m/z=451.1 (M+1)$^+$.

Compound 7c: The triflate 6c (8.0 g, 0.0178 mol) was dissolved in 250 mL of toluene/ethanol (4:1) and treated with 3-cyanophenyl boronic acid (3.1 g, 0.021 mol, 1.2 eq) and sodium carbonate solution (2M aq. solution, 21 mL). The reaction mixture was degassed for 10 minutes and treated with tetrakistriphenylphosphine palladium (1.0 g, 5 mol %). The reaction was heated at 80° C. overnight. The solid particles were filtered off through a small pad of celite and washed with ethyl acetate. The solvent was removed in vacuo and the product was isolated by SiO$_2$ chromatography using 3–10% methanol/dichloromethane as eluent. ES MS: calcd for $C_{25}H_{30}N_3O_2^+$ m/z=404.23; found m/z=404.1 (M+1)$^+$.

Compound 8c: Compound 7c (2.78 g, 0.0069 mmol) was dissolved in 30 mL of acetonitrile and treated with 2.11 g (2.0 eq) of methyl bromoacetate, 2.24 g (1 eq) of Cs$_2$CO$_3$. The reaction was heated in a sealed tube at 150° C. for 3 hours. The solvent was removed in vacuo and the and the product was isolated by SiO$_2$ column using 30–40% ethyl acetate/hexane as eluent to afford 0.34 g of compound 8c. ES MS: calcd for $C_{28}H_{34}N_3O_4^+$ m/z=476.25; found m/z=476.1 (M+1)$^+$.

Compound 9c: To a suspension of NaH (0.143 g, 5 eq) in toluene (10 mL) was added 3,5-dichloroaniline (0.23 g, 2 eq) and stirred the mixture at room temperature for 15 minutes. The methyl ester 8c (0.34 g, 0.715 mol) was added to the above solution and heated under reflux overnight. The reaction was quenched by the addition of water and extracted with ethyl acetate. The organic layer was washed with brine and dried over sodium sulfate. The solvent was removed in vacuo and the product was isolated by SiO$_2$ chromatography using 20–30% ethyl acetate/hexane as eluent to afford 0.2 g of compound 9c. ES MS: calcd for C$_{33}$H$_{35}$Cl$_2$N$_4$O$_3^+$ m/z=605.21; found m/z=605.1 (M+1)$^+$.

The following compounds could be similarly prepared via amidation of the corresponding esters:

| Cpd # | STRUCTURE | ANALYTICAL DATA |
|---|---|---|
| 8b | 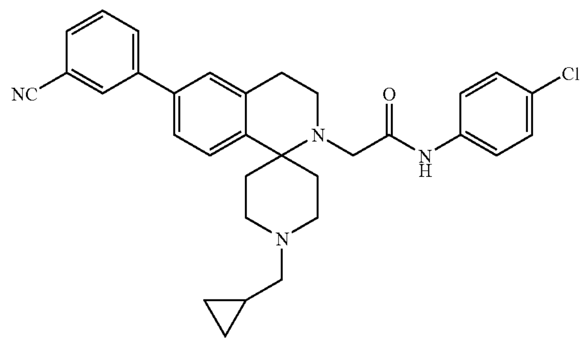 | ES MS: calcd for C$_{32}$H$_{34}$ClN$_4$O$^+$ m/z = 525.24; found m/z = 525.1 (M + 1)$^+$ |
| 8c | 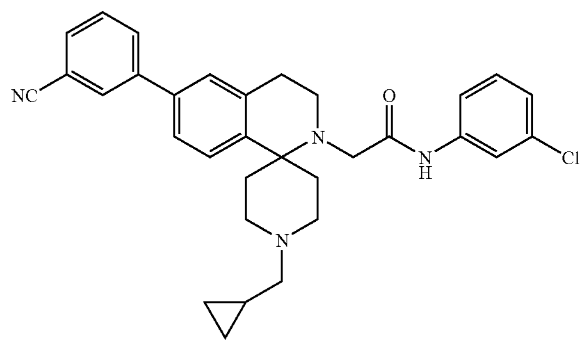 | ES MS: calcd for C$_{32}$H$_{34}$ClN$_4$O$^+$ m/z = 525.24; found m/z = 525.1 (M + 1)$^+$ |
| 8d | 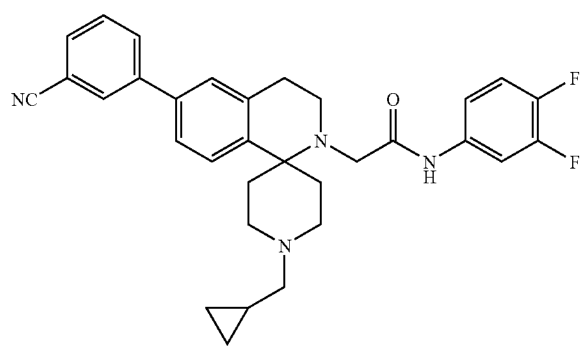 | ES MS: calcd for C$_{32}$H$_{33}$F$_2$N$_4$O$^+$ =527.26; found m/z = 527.1 (M + 1)$^+$ |
| 8e | 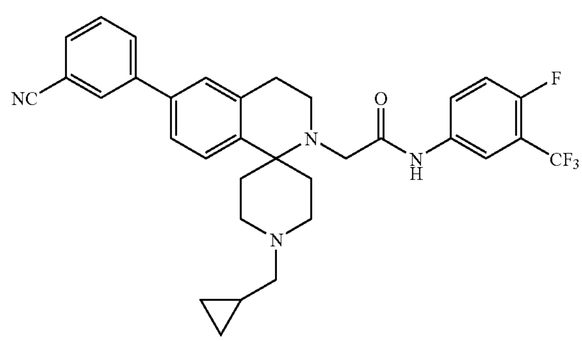 | ES MS: calcd for C$_{33}$H$_{33}$F$_4$N$_4$O$^+$ m/z = 577.25; found m/z = 577.1 (M + 1)$^+$ |

-continued

| Cpd # | STRUCTURE | ANALYTICAL DATA |
|---|---|---|
| 8f | 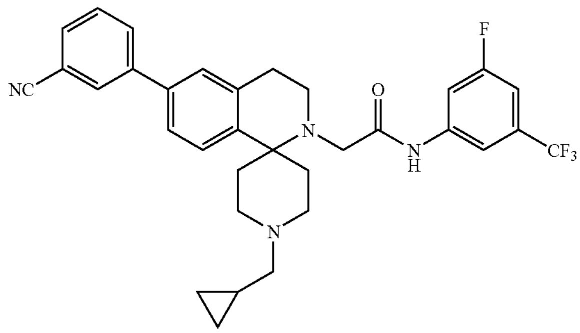 | ES MS: calcd for $C_{33}H_{33}F_4N_4O^+$ = 577.25; found m/z = 577.1 (M + 1)$^+$ |
| 8g | 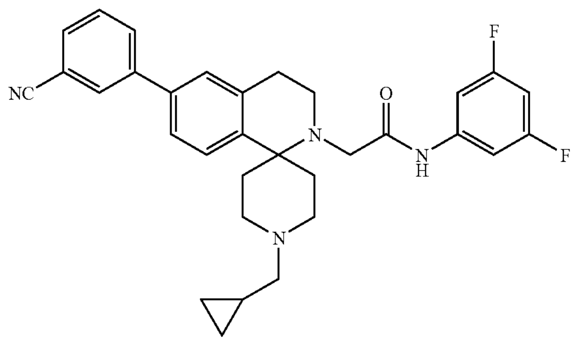 | ES MS: calcd for $C_{32}H_{33}F_2N_4O^+$ m/z = 527.26; found m/z = 527.1 |
| 8h | 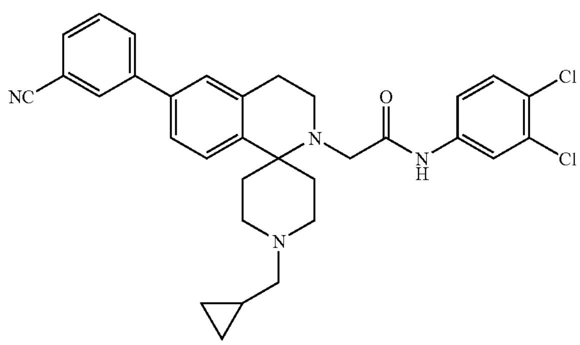 | ES MS: calcd for $C_{32}H_{33}Cl_2N_4O^+$ m/z = 559.2; found m/z = 559.1 |
| 8i | 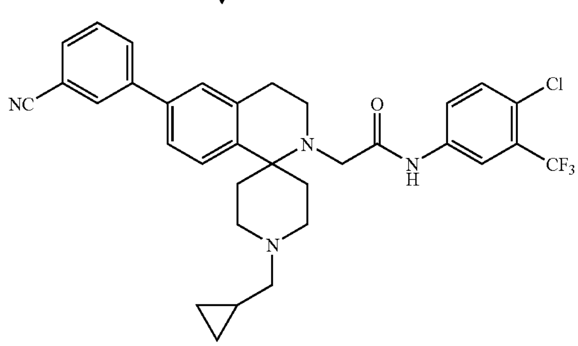 | ES MS: calcd for $C_{33}H_{33}ClF_3N_4O^+$ m/z = 593.23; found m/z = 593.1 |

Compound 10c: To a solution of compound 9c in dichloromethane (2 mL) was added TFA (1 mL) and the contents were stirred at room temperature for 2 hours. The reaction mixture was quenched by the addition of sodium bicarbonate solution and extracted with dichloromethane. The solvent was removed in vacuo and the product was isolated by SiO$_2$ chromatography using 4% methanol/dichloromethane as eluent to afford 0.117 g of compound 10c. ES MS: calcd for $C_{28}H_{27}Cl_2N_4O^+$ m/z=505.16; found m/z=505.1 (M+1)$^+$.

Compound 11a: To a solution of compound 10c (0.022 g) in DCM (1 mL) was added cycloheptanone (0.02 mL, excess) and triacetoxy sodium borohydride (0.015 g, 3 eq) and the contents were stirred overnight. Amberlyst 15 was added to the reaction mixture and shaken for 3 hours. The resin was washed three times with MeOH, DCM and THF. The product was eluted from the resin using 2N ammonia in MeOH. The solvent was removed in vacuo to afford 2 mg of compound 11a. ES MS: calcd for $C_{35}H_{39}Cl_2N_4O^+$ m/z=601.25; found m/z=601.1 (M+1)$^+$.

| 11a | 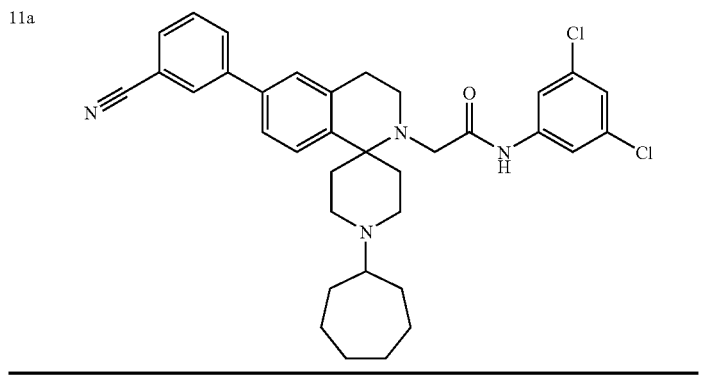 |
|---|---|

The following compounds could be prepared by a similar reductive alkylations of spiropiperidine 10c:

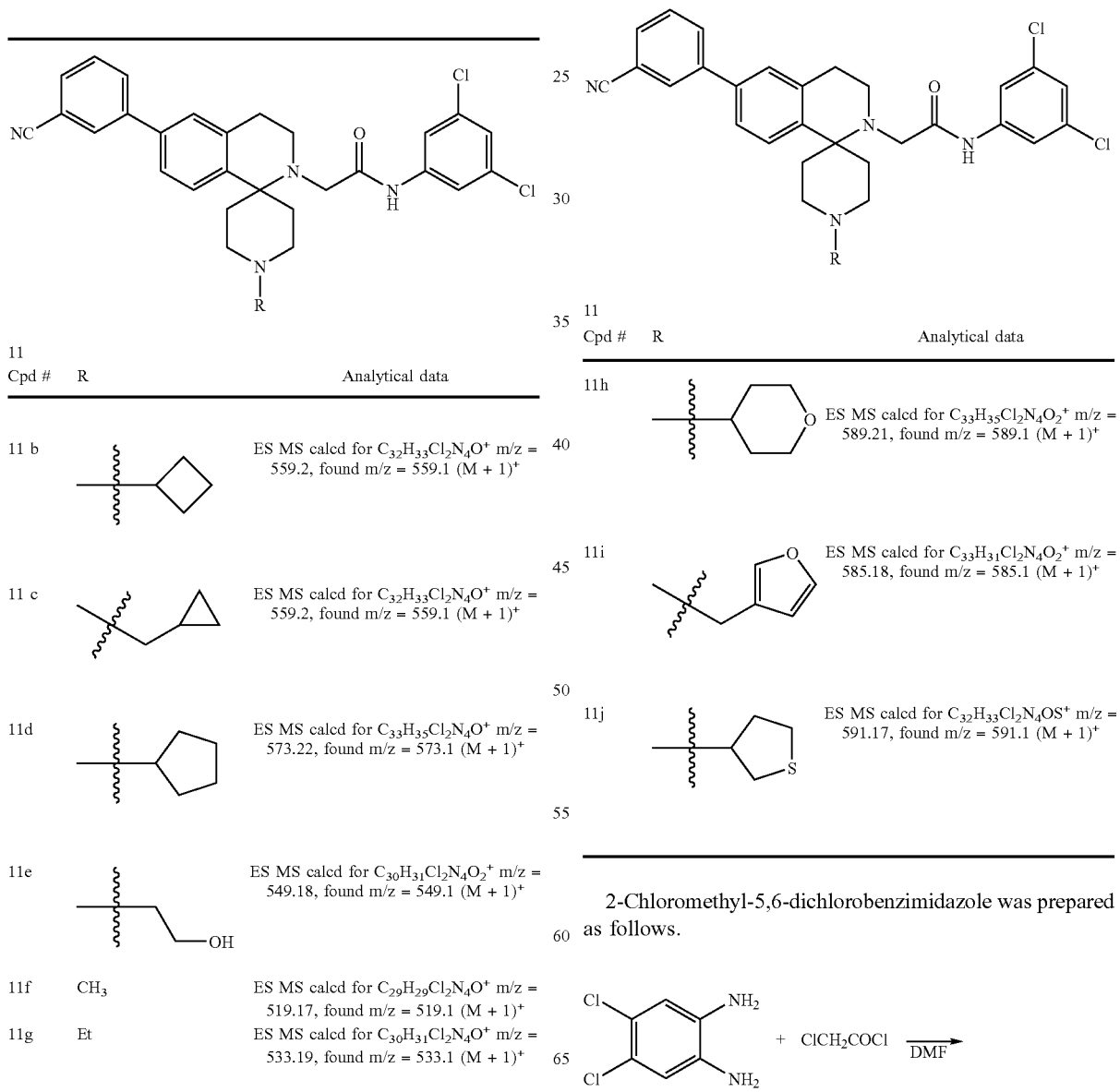

| Cpd # | R | Analytical data |
|---|---|---|
| 11b | cyclobutyl | ES MS calcd for $C_{32}H_{33}Cl_2N_4O^+$ m/z = 559.2, found m/z = 559.1 $(M + 1)^+$ |
| 11c | cyclopropylmethyl | ES MS calcd for $C_{32}H_{33}Cl_2N_4O^+$ m/z = 559.2, found m/z = 559.1 $(M + 1)^+$ |
| 11d | cyclopentyl | ES MS calcd for $C_{33}H_{35}Cl_2N_4O^+$ m/z = 573.22, found m/z = 573.1 $(M + 1)^+$ |
| 11e | —CH(CH$_3$)CH$_2$OH | ES MS calcd for $C_{30}H_{31}Cl_2N_4O_2^+$ m/z = 549.18, found m/z = 549.1 $(M + 1)^+$ |
| 11f | CH$_3$ | ES MS calcd for $C_{29}H_{29}Cl_2N_4O^+$ m/z = 519.17, found m/z = 519.1 $(M + 1)^+$ |
| 11g | Et | ES MS calcd for $C_{30}H_{31}Cl_2N_4O^+$ m/z = 533.19, found m/z = 533.1 $(M + 1)^+$ |
| 11h | tetrahydropyran-4-yl | ES MS calcd for $C_{33}H_{35}Cl_2N_4O_2^+$ m/z = 589.21, found m/z = 589.1 $(M + 1)^+$ |
| 11i | furan-3-ylmethyl | ES MS calcd for $C_{33}H_{31}Cl_2N_4O_2^+$ m/z = 585.18, found m/z = 585.1 $(M + 1)^+$ |
| 11j | tetrahydrothiophen-3-yl | ES MS calcd for $C_{32}H_{33}Cl_2N_4OS^+$ m/z = 591.17, found m/z = 591.1 $(M + 1)^+$ |

2-Chloromethyl-5,6-dichlorobenzimidazole was prepared as follows.

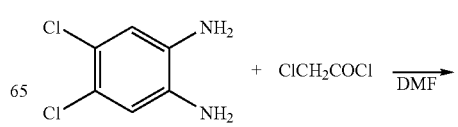

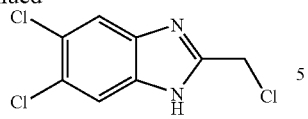 5

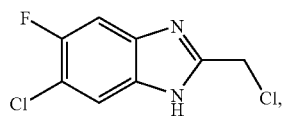

To a solution of 1,2-diamino-4,5-dichlorobenzene (3.0 g. 0.0169 mol) in DMF (30 mL) was added chloroacetyl chloride (2.7 mL, 2 eq) dropwise at 0oC and stirred at that temperature for 30 minutes. The reaction mixture was warmed to room temperature and stirred for 1 hour. The reaction mixture was poured into ice water and the solid was filtered. The solid was washed several times with water and dried in air. ES MS Calcd for $C_8H_6Cl_3N_2^+$ m/z=234.96, found m/z=326.1 (M+1)+.

Similarly, 2-chloromethyl-5-chloro-6-fluorobenzimidazole, was also prepared starting from 1,2-diamino-4-chloro-5-fluorobenzene: ES MS calcd for $C_8H_6Cl_2FN_2^+$ m/z=218.99, obsd m/z=219.1 (M+1)+.

These two alkylating agents were used to prepare the following analogous benzimidazole compounds using alkylation procedure F. The piperidine NH analogs, 12d and 12e were prepared by alkylation of the N-Boc intermediate, followed by TFA deprotection of the N-Boc group. Analog 12f was prepared by reductive alkylation of compound 12d following the procedure B above.

| Cpd # | STRUCTURE | ANALYTICAL DATA |
|---|---|---|
| 12a | 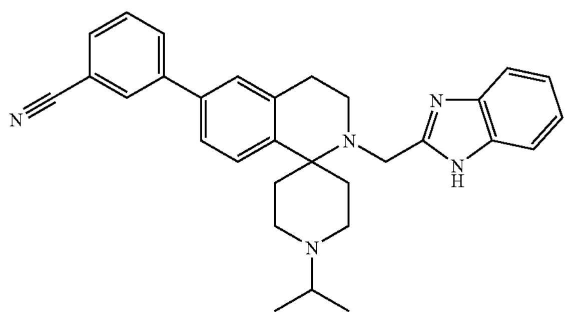 | ES MS: calcd for $C_{31}H_{34}N_5^+$ m/z = 476.63; found m/z = 476.1 (M + 1)+ |
| 12b | 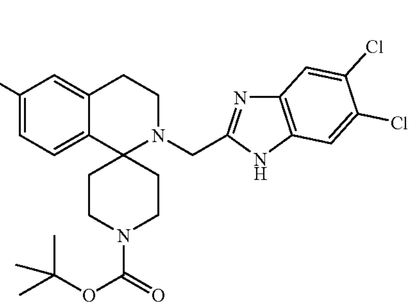 | ES MS: calcd for $C_{33}H_{34}Cl_2N_5O_2^+$ m/z= 602.21; found m/z = 602.3 (M + 1)+ |
| 12c | 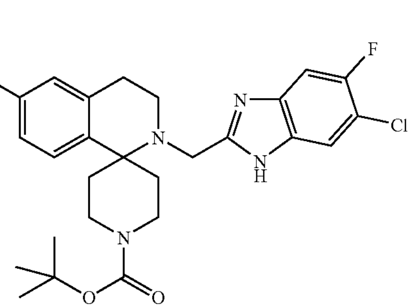 | ES MS: calcd for $C_{33}H_{34}ClFN_5O_2^+$ m/z= 586.24; found m/z = 586.1 (M + 1)+ |

| Cpd # | STRUCTURE | ANALYTICAL DATA |
|---|---|---|
| 12d | 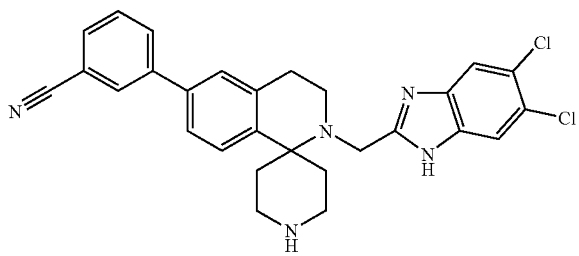 | ES MS: calcd for $C_{28}H_{26}Cl_2N_5^+$ m/z = 502.16; found m/z = 502.1 $(M+1)^+$ |
| 12e | 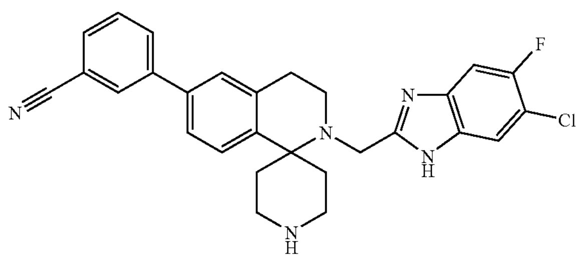 | ES MS: calcd for $C_{28}H_{26}ClFN_5^+$ m/z = 486.19; found m/z = 486.1 $(M+1)^+$ |
| 12f | 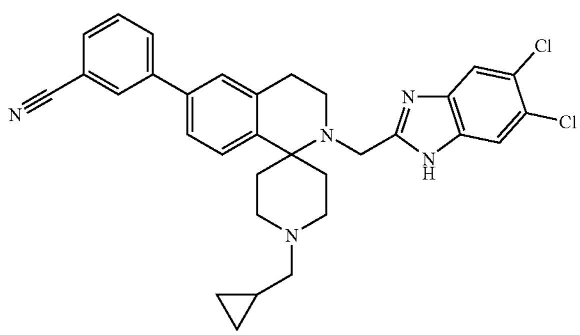 | ES MS: calcd for $C_{32}H_{32}Cl_2N_5^+$ m/z = 556.20; found m/z = 556.1 $(M+1)^+$ |
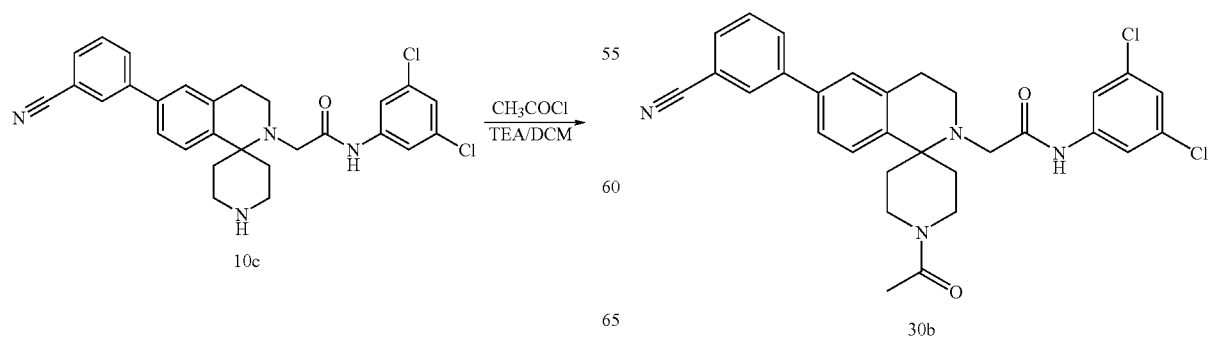

Compound 30b: To a solution of spirocyclic piperazine compound 10c (0.02g, 0.04 mmol) in dichloromethane (1 mL) was added triethylamine (0.05 mL, 10 eq) followed by acetyl chloride (0.029 mL, 10 eq) at room temperature. The reaction mixture was stirred overnight at room temperature and the product was isolated by prep TLC using 5% methanol in dichloromethane as eluent.

ES MS: calcd for $C_{30}H_{29}Cl_2N_4O_2^+$ m/z=547.17; found m/z=547.1 (M+1)$^+$.

Compounds 30a, 30c and 30d can be prepared by analogous methods well known in the art.

MGCl$_2$, 10 mM NaCl, 5 mM MnCl$_2$, 0.1% BSA). The membrane/bead mixture was centrifuged (1500×g, 3.5 min), the supernatant was aspirated, and the pellet was resuspended in 10 ml binding buffer. The centrifugation, aspiration and resuspension were then repeated. The membrane/bead mixture (100 μl) was then added to 96-well plates containing 50 μof 500 pM [$^{125}$I]-MCH (NEN) and 50 ml of the appropriate concentration of compound (4× the desired final concentration). Nonspecific binding was determined by including 1 μM MCH in the binding reaction. The binding reaction was incubated at room temperature for 2 h. Plates

| Cpd # | STRUCTURE | ANALYTICAL DATA |
|---|---|---|
| 30a | 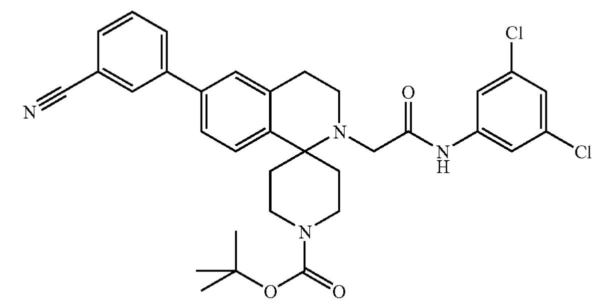 | ES MS: calcd for $C_{33}H_{35}Cl_2N_4O_3^+$ m/z = 605.21; found m/z = 605.1 (M + 1)$^+$ |
| 30c | 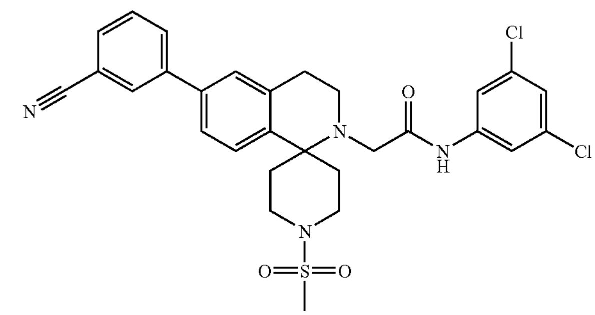 | ES MS: calcd for $C_{29}H_{29}Cl_2N_4O_3S^+$ m/z = 583.13; found m/z = 583.1 (M + 1)$^+$ |
| 30d | 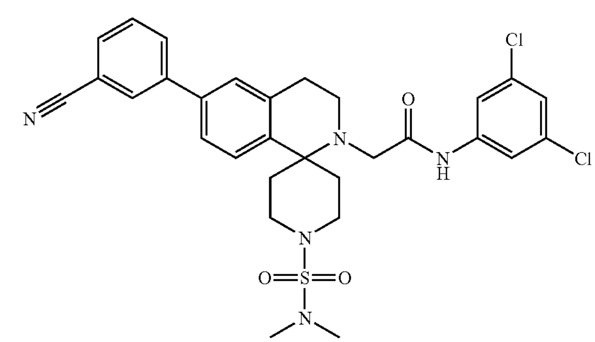 | ES MS: calcd for $C_{30}H_{32}Cl_2N_5O_3S^+$ m/z = 612.16; found m/z = 612.1 (M + 1)$^+$ |

MCH Receptor Binding Assay:

Membranes from CHO cells expressing the MCH receptor were prepared by lysing cells with 5 mM HEPES for 15 min at 4C. Cell lysates were centrifuged (12.5000×g, 15 min) and the pellet was resuspended in 5 mM HEPES. For each 96-well plate (Microlite, Dynex Technologies), 1 mg of cell membranes were incubated with 10 mg of wheat germ agglutinin SPA beads (Amersham) for 5 min at 4 C in a volume of 10 ml of binding buffer (25 mM HEPES, 10 mM were then analyzed in a TOPCOUNT microplate scintillation counter (Packard). Data was analyzed and Ki values were determined using GraphPad Prism.

Compounds with Ki values greater than 100 nM are designated in the table below as C class compounds.

Compounds with Ki values between 30 and 100 nM are designated in the table below as B class compounds.

Compounds with Ki values less than 30 nM are designated in the table below as A class compounds.

In a preferred embodiment of the invention, Example 11a, a Ki value of 11 nM was observed.

| Cpd # | Activity |
|---|---|
| 8b | C |
| 8c | B |
| 8d | B |
| 8e | A |
| 8f | B |
| 7d | C |
| 7b | B |
| 7c | B |
| 7a | A |
| 7e | C |
| 8a | A |
| 10c | B |
| 11c | A |
| 11d | A |
| 11e | B |
| 11f | B |
| 11g | B |
| 8g | B |
| 8h | C |
| 8i | C |
| 11h | A |
| 11i | B |
| 11b | A |
| 11j | B |
| 11a | A |
| 12a | C |
| 12d | C |
| 12e | C |
| 12f | C |
| 30a | C |
| 30b | C |
| 30c | C |
| 30d | C |

What is claimed is:

1. A compound represented by the structural formula

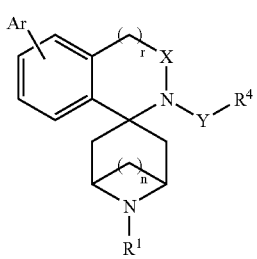

formula I or a pharmaceutically acceptable salt or solvate wherein
X is —$CH_2$—, —$SO_2$—, carbonyl, —$CHCH_3$ or —$C(CH_3)_2$—;
Y is —$(CR^2R^3)_pC(O)NH$—, wherein p is a number from 1 to 3 and when p is more than 1, each $(CR^2R^3)$ can be the same or different;
n is 0, such that no connecting bond exists between the two carbons adjacent to the nitrogen;
r is 1;
Ar is aryl or $R^6$-substituted aryl;
$R^1$ is hydrogen, methyl, ethyl, hydroxyethyl, cyclobutyl, cyclopentyl, cycloheptyl, -propyl, —$SO_2CH_3$, —$SO_2N(CH_3)_2$, —$COCH_3$, —$C(O)OC(CH_3)_3$, isopropyl, cyclopropylmethyl,

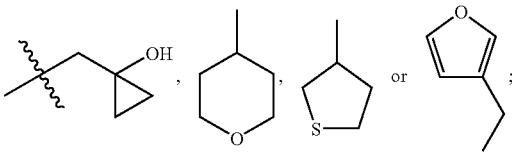

$R^2$ and $R^3$ can be the same or different, each being independently hydrogen or -alkyl; or $R^2$ and $R^3$ can be joined together with the carbon to which they are attached to form a 3 to 7-membered ring;
$R^4$ is aryl, $R^7$-substituted aryl, or Y—$R^4$ is

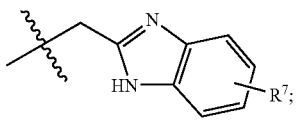

$R^5$ is -alkyl, aryl, aralkyl or heteroaryl;
$R^6$ is 1 to 3 substituents, each $R^6$ can be the same or different and each is independently selected from the group consisting of —OH, -alkoxy, —$OCF_3$, —CN, -alkyl, halogen, —$NR^8R^9$, —$C(O)NR^8R^9$, —$NR^8SO_2R^5$, —$SO_2NR^8R^9$, —$SO_2R^5$, —$C(O)R^5$, —$C(O)OR^5$, —$CF_3$, —$(CR^2R^3)_{p''}NR^8R^9$ where p" is a number from 1 to 3, —CHO, —C=$NOR^8$, —$NR^8C(O)R^5$, —C(=NH)$NR^8R^9$, —C(=NCN)$NR^8R^9$,

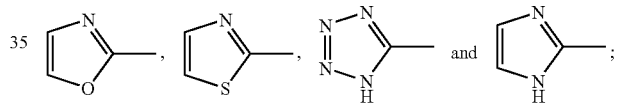

$R^7$ is hydrogen or 1 to 4 substituents, each $R^7$ can be the same or different and each is independently selected from the group consisting of —OH, -alkoxy, —$OCF_3$, —CN, halogen, -nitro, —$NR^8R^9$, —$NR^8C(O)R^5$, —$C(O)NR^8R^9$, —$NR^8SO_2R^5$, —$SO_2NR^8R^9$, —$SO_2R^5$, —$C(O)R^5$, —$C(O)OR^8$, —$CF_3$, —$(CR^2R^3)_{p''}NR^8R^9$, —$(CR^2R^3)_{p''}NR^8C(O)R^5$ where p" is a number from 1 to 3, —C(=NH)$NR^8R^9$, —C(=NCN)$NR^8R^9$ and —CHO; or two adjacent $R^7$ groups can be joined together to form a methylenedioxy or ethylenedioxy group;
$R^8$ is hydrogen or -alkyl;
$R^9$ is hydrogen, -alkyl, aryl, substituted aryl, heteroaryl or aralkyl; and
$R^{10}$ is —OH, -alkoxy, -cycloalkyl, -cycloalkylalkyl, —$C(O)NR^8R^9$, —$NR^8R^9$, —$NR^8SO_2R^5$, —$NR^8C(O)R^5$, —$NR^8C(O)OR^5$, —$NR^8C(O)NR^8R^9$, —C(O)OH or —$C(O)OR^5$.

2. The compound of claim 1 wherein
X is —$SO_2$—;
$R^2$ and $R^3$ are hydrogen or alkyl; and
n is 0.

3. The compound of claim 2 wherein $R^2$ and $R^3$ are hydrogen.

4. The compound of claim 1 wherein
X is carbonyl;
$R^2$ and $R^3$ are hydrogen or alkyl; and
n is 0.

5. The compound of claim 4 wherein $R^2$ and $R^3$ are hydrogen.

6. The compound of claim 1 wherein
X is —CH$_2$—;
$R^1$ is hydrogen, -alkyl, -cycloalkyl, -cycloalkylalkyl, heteroaralkyl, heterocyclyl, -alkyl substituted with -cycloalkyl, -alkyl substituted with $R^{10}$, —SO$_2$NR$^8$R$^9$, —SO$_2$R$^5$; —C(O)R$^5$ or —C(O)OR$^5$;
$R^2$ and $R^3$ are hydrogen or alkyl;
n is 0;
and
Ar is aryl or $R^6$-substituted aryl.

7. The compound of claim 6 wherein
$R^1$ is hydrogen, methyl, ethyl, hydroxyethyl, cyclobutyl, cyclopentyl, cycloheptyl, -propyl, —SO$_2$CH$_3$, —SO$_2$N(CH$_3$)$_2$, —COCH$_3$, —C(O)OC(CH$_3$)$_3$, isopropyl, cyclopropylmethyl, heteroaryl,

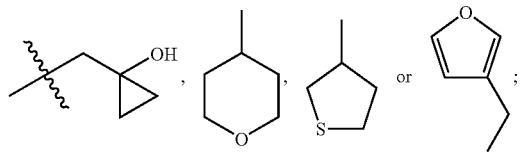

$R^2$ and $R^3$ are hydrogen;
Ar is $R^6$-substituted aryl;
$R^6$ is 1 to 5 substituents which can be the same or different and each is independently selected from the group consisting of halogen, —CF$_3$, —OCF$_3$, —CN, —CHO, —SO$_2$R$^5$, —C(O)OR$^8$, —C(O)R$^5$, —C(O)NR$^8$R$^9$ and

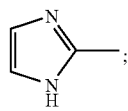

and
$R^7$ is two substituents which can be the same or different and independently selected from halogen, —CN and —CF$_3$.

8. The compound of claim 7 wherein $R^6$ is one substituent.
9. The compound of claim 8 wherein $R^6$ is at the meta position of Ar.
10. The compound of claim 9 wherein $R^6$ is —CN.
11. The compound of claim 9 wherein $R^6$ is —C(=NH)NHaryl or —C(=NH)NH$_2$.
12. The compound of claim 10 wherein $R^7$ is selected from the group consisting of Cl, F and —CF$_3$.
13. The compound of claim 12 wherein $R^1$ is hydrogen, methyl, ethyl, hydroxyethyl, cyclobutyl, cyclopentyl, cycloheptyl, -propyl, —SO$_2$CH$_3$, —SO$_2$N(CH$_3$)$_2$, —COCH$_3$, —C(O)OC(CH$_3$)$_3$, isopropyl, cyclopropylmethyl,

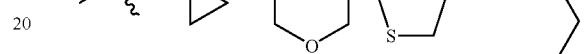

14. The compound of claim 1 wherein
X is —CH$_2$—;
Y—R$^4$ is

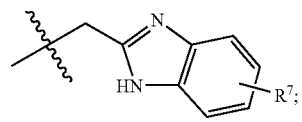

n is 0;
Ar is $R^6$-substituted aryl;
$R^1$ is alkyl or cyclopropylmethyl;
$R^6$ is —CN and is substituted at the meta position of Ar; and
$R^7$ is hydrogen or halogen.

15. The compound of claim 14 wherein $R^7$ is chloride or fluoride.

16. A compound selected from the group consisting of

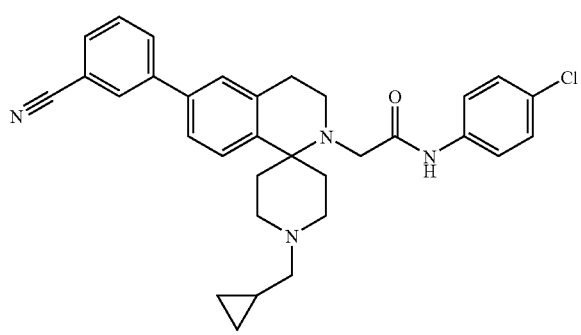

8b

-continued
8c
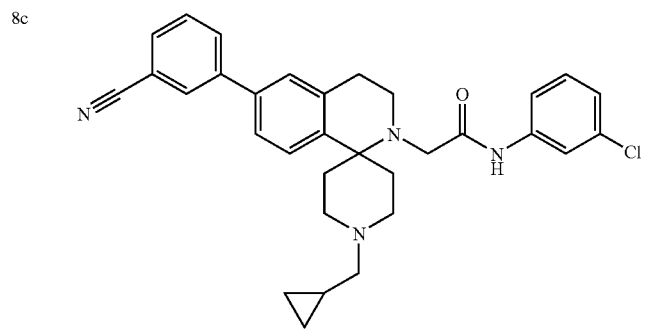
8d
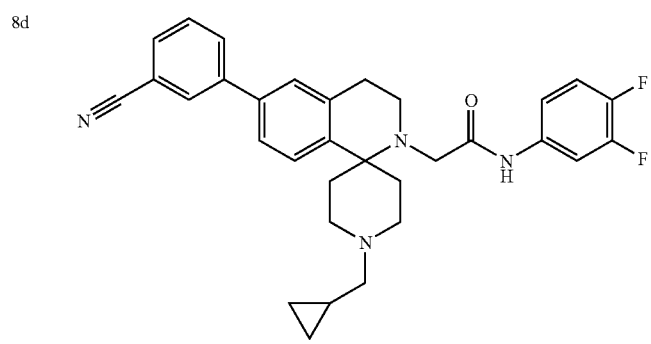
8e
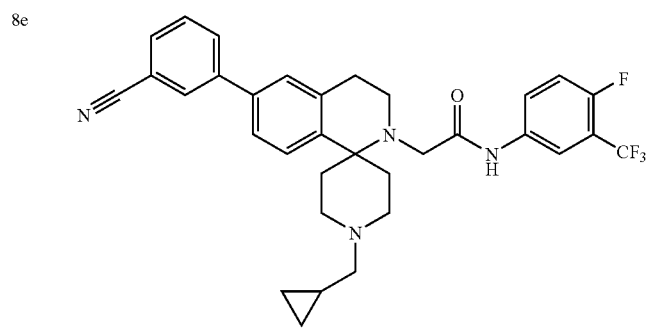
8f
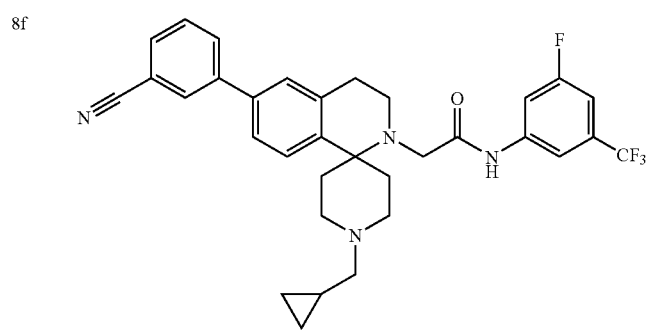
7d
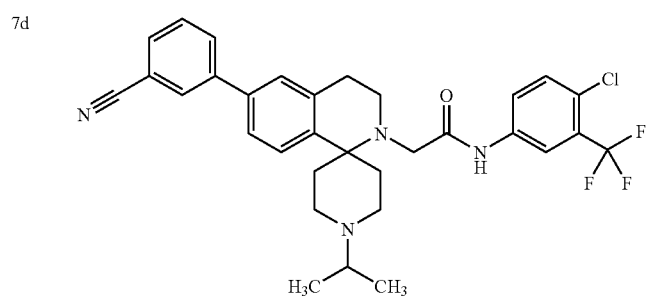

-continued
7b
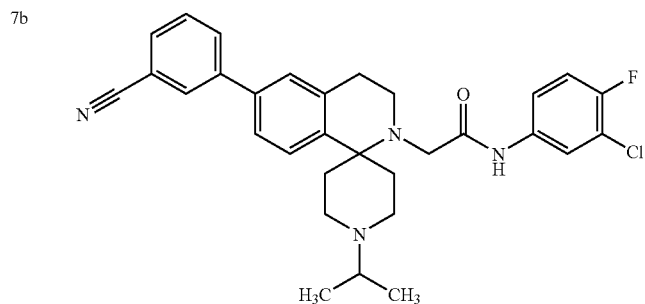
7c
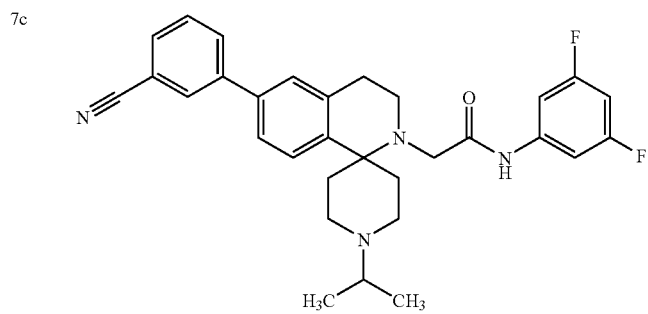
7a
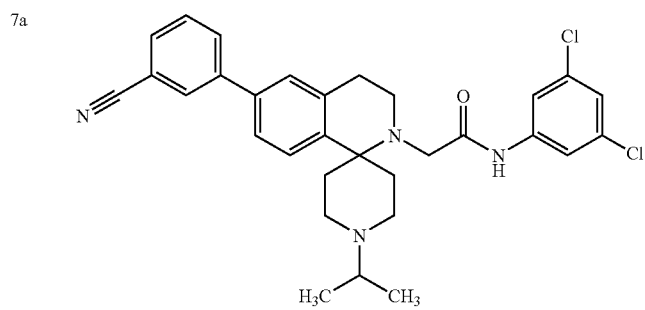
7e
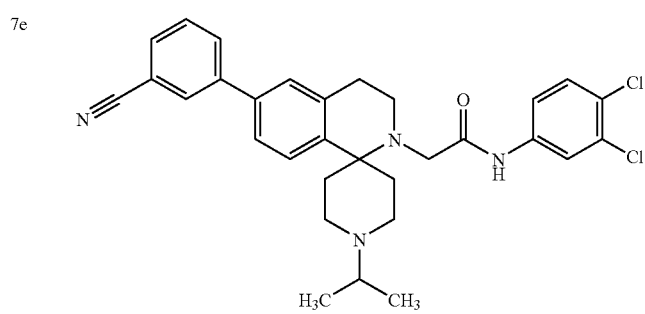
8a
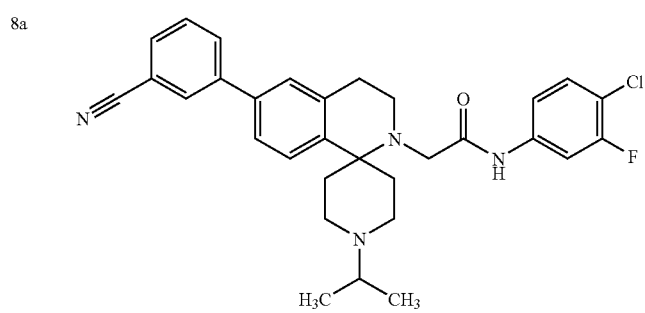

-continued
10c
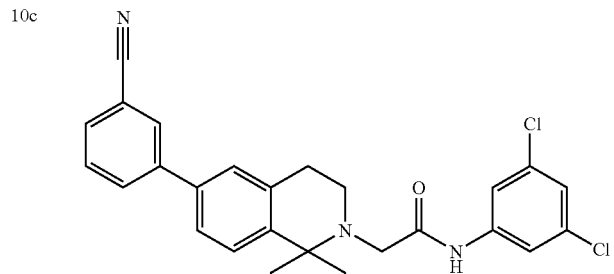
11c
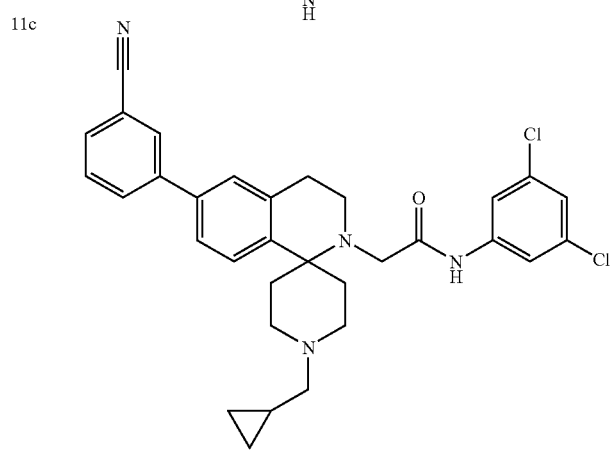
11d
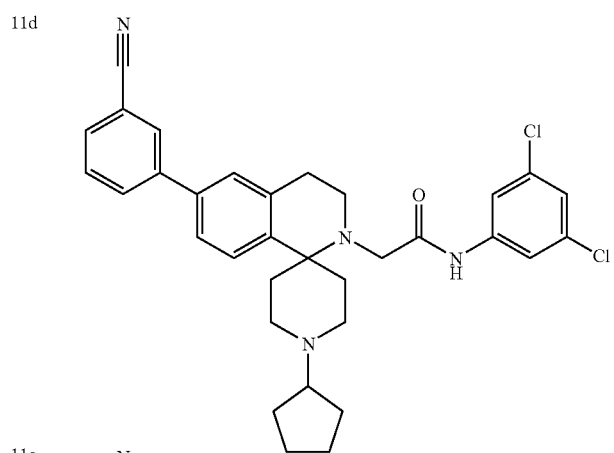
11e
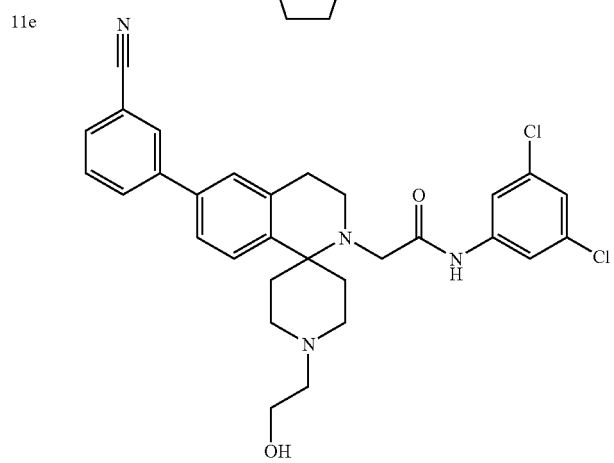

-continued
11f
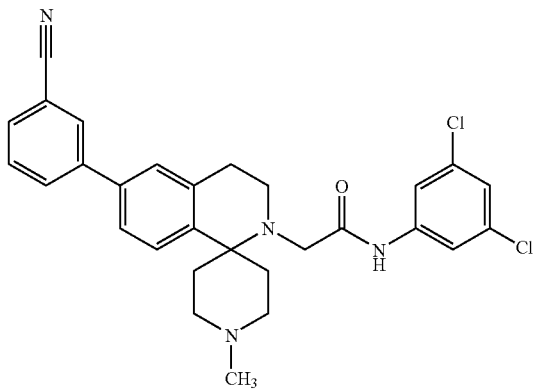
11g
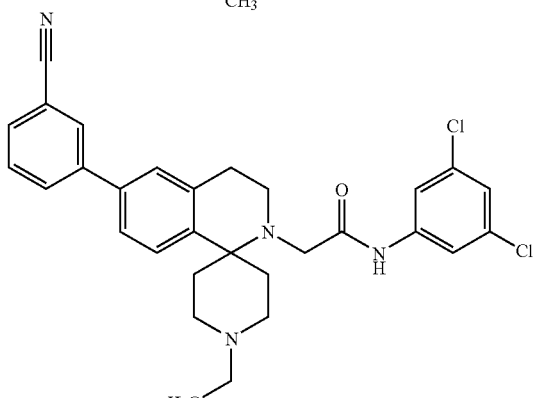
8g
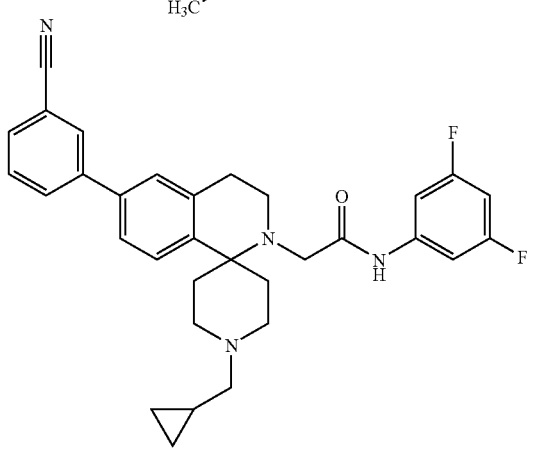
8h
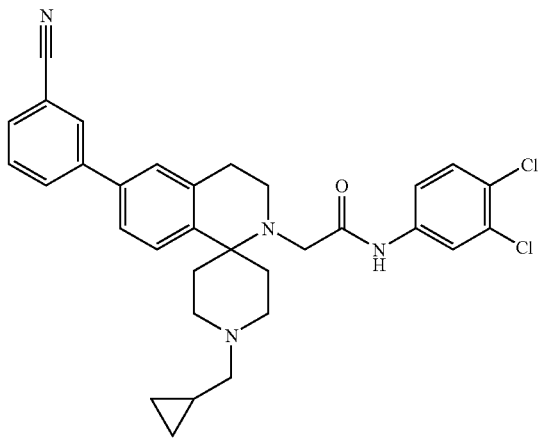

8i
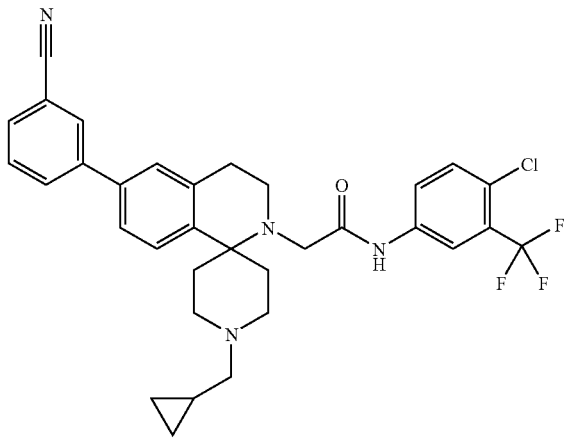
11h
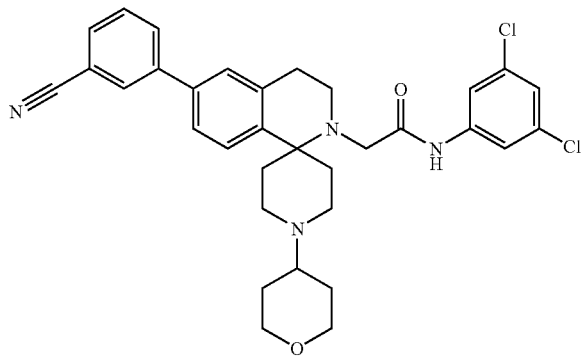
11i
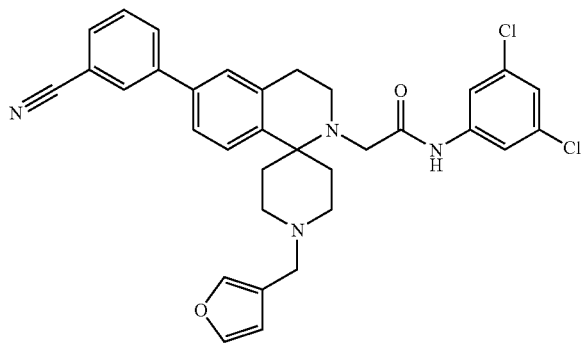
11b
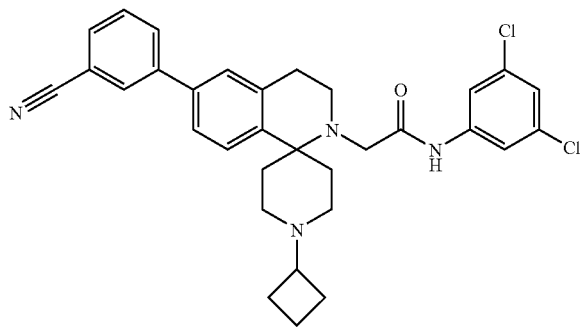

-continued
11j
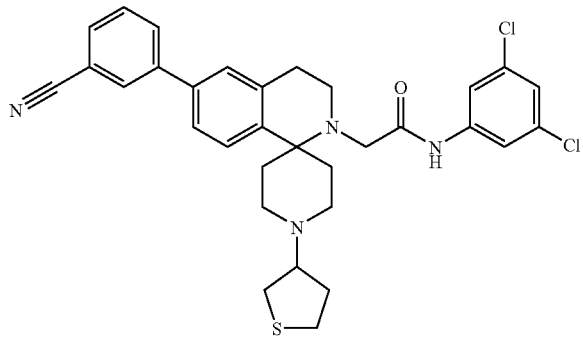
11a
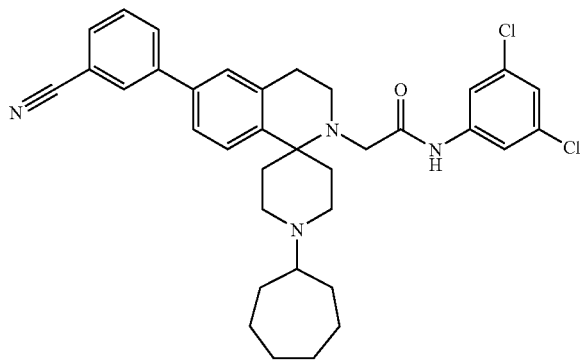
12a
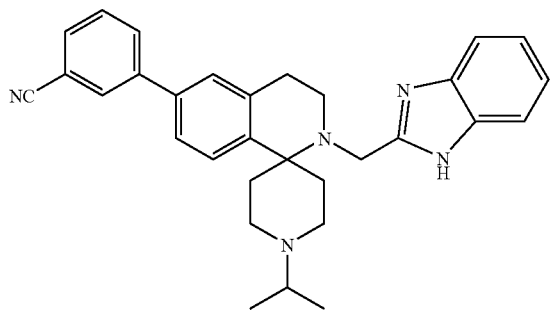
12d
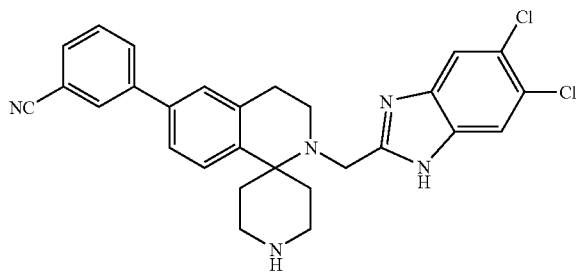
12e
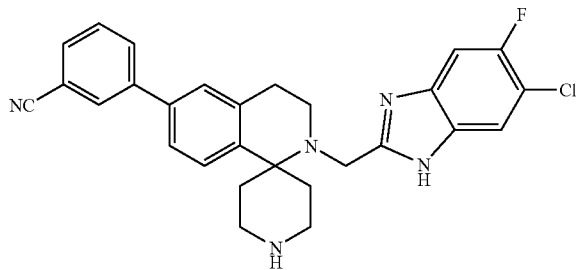

-continued
12f
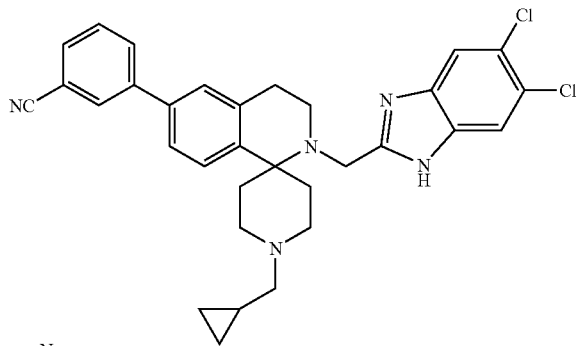
30a
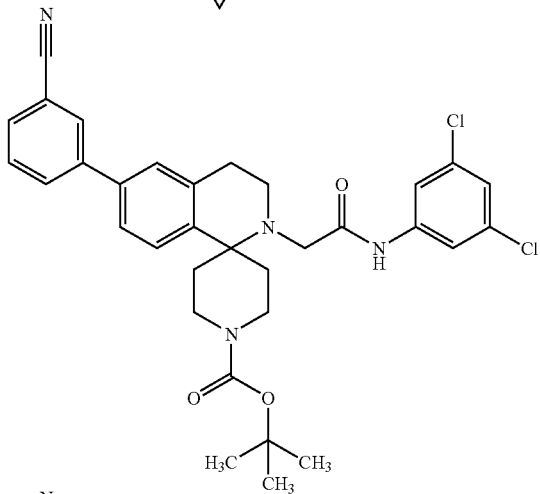
30b
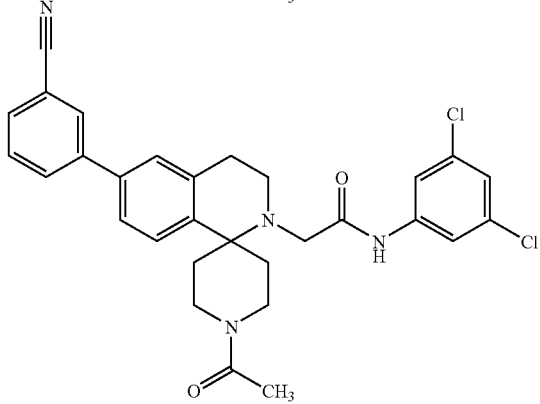
30c
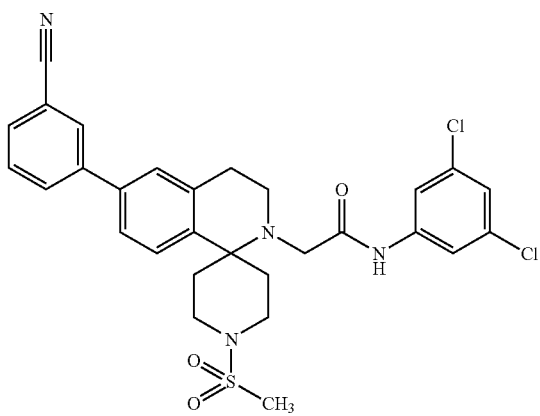

and 30d

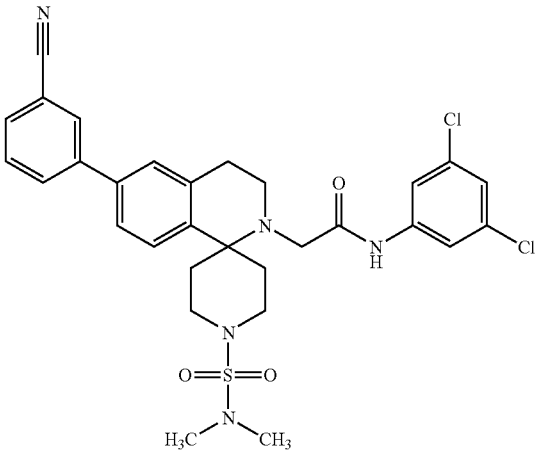

or a pharmaceutically acceptable salt or solvate.

17. A pharmaceutical composition comprising a therapeutically effective amount of at least one compound of claim 1 in combination with at least one pharmaceutically acceptable carrier.

18. A method of treating obesity, hyperphagia or diabetes comprising administering a therapeutically effective amount of at least one compound of claim 1 to a patient in need of such treatment.

19. A method of treating hyperphagia comprising administering to a patient in need of such treatment a therapeutically effective amount of at least one compound of claim 1, or a pharmaceutically acceptable salt or solvate of said compound.

20. A pharmaceutical composition comprising a therapeutically effective amount of at least one compound of claim 16 in combination with at least one pharmaceutically acceptable carrier.

21. A method of treating obesity, hyperphagia or diabetes comprising administering a therapeutically effective amount of at least one compound of claim 16 to a patient in need of such treatment.

22. A method of treating hyperphagia comprising administering to a patient in need of such treatment a therapeutically effective amount of at least one compound of claim 16, or a pharmaceutically acceptable salt or solvate of said compound.

* * * * *

UNITED STATES PATENT AND TRADEMARK OFFICE
CERTIFICATE OF CORRECTION

PATENT NO.         : 7,109,207 B2
APPLICATION NO. : 10/607051
DATED              : September 19, 2006
INVENTOR(S)       : Duane A. Burnett et al.

It is certified that error appears in the above-identified patent and that said Letters Patent is hereby corrected as shown below:

In the Claims:

Claim 16, col. 49 bottom, Formula 8a:   Please correct the formula:

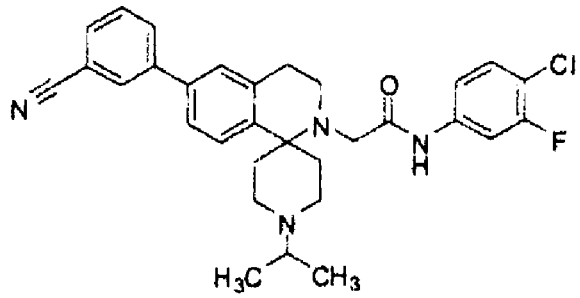

to

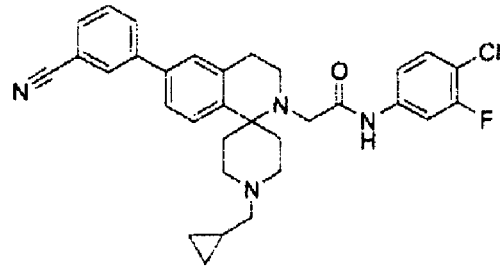

Signed and Sealed this

Third Day of June, 2008

JON W. DUDAS
*Director of the United States Patent and Trademark Office*